(12) United States Patent
Dodge et al.

(10) Patent No.: US 8,476,300 B2
(45) Date of Patent: Jul. 2, 2013

(54) SELECTIVE ESTROGEN RECEPTOR MODULATOR FOR THE TREATMENT OF OSTEOARTHRITIS

(75) Inventors: Jeffrey Alan Dodge, Indianapolis, IN (US); Timothy Ivo Richardson, Zionsville, IN (US); Christian Alexander Clarke, Fishers, IN (US); Scott Alan Jones, Indianapolis, IN (US); Ronald Jay Hinklin, Longmont, CO (US); Conrad Wilson Hummel, Louisville, CO (US); George Sal Lewis, Louisville, CO (US)

(73) Assignee: Eli Lilly and Company, Indianapolis, IN (US)

( * ) Notice: Subject to any disclaimer, the term of this patent is extended or adjusted under 35 U.S.C. 154(b) by 173 days.

(21) Appl. No.: 13/062,272

(22) PCT Filed: Sep. 3, 2009

(86) PCT No.: PCT/US2009/055805
§ 371 (c)(1),
(2), (4) Date: Mar. 4, 2011

(87) PCT Pub. No.: WO2010/036497
PCT Pub. Date: Apr. 1, 2010

(65) Prior Publication Data
US 2011/0166182 A1    Jul. 7, 2011

Related U.S. Application Data

(60) Provisional application No. 61/100,983, filed on Sep. 29, 2008, provisional application No. 61/118,759, filed on Dec. 1, 2008.

(51) Int. Cl.
*A61K 31/4453* (2006.01)
*C07D 211/06* (2006.01)

(52) U.S. Cl.
USPC .......................................... 514/319; 546/206

(58) Field of Classification Search
USPC .......................................... 514/319; 546/206
See application file for complete search history.

(56) References Cited

U.S. PATENT DOCUMENTS 5,484,795 A * 1/1996 Bryant et al. ................. 514/319
5,589,482 A   12/1996 Thompson

FOREIGN PATENT DOCUMENTS

| EP | 0729951 | 9/1996 |
| WO | 0224653 | 3/2002 |
| WO | 2004009086 | 1/2004 |
| WO | 2005073204 | 8/2005 |
| WO | 2006002185 | 1/2006 |

OTHER PUBLICATIONS

King, Med. Chem. Principle and Practice (1994), pp. 206-208.*

* cited by examiner

*Primary Examiner* — Taofiq A Solola
(74) *Attorney, Agent, or Firm* — MaCharri Vorndran-Jones

(57) ABSTRACT

The present invention is directed to a compound of the formula (A): or a pharmaceutically acceptable salt thereof; and also to compounds of formula (I): or a pharmaceutically acceptable salt thereof.

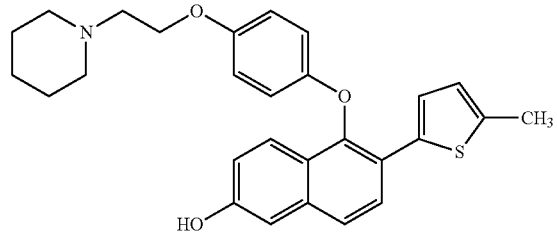

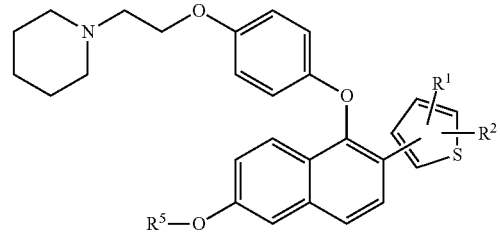

14 Claims, No Drawings

SELECTIVE ESTROGEN RECEPTOR MODULATOR FOR THE TREATMENT OF OSTEOARTHRITIS

REFERENCE TO RELATED APPLICATION

This application is submitted as a United States national phase entry, pursuant to 35 USC §371 of PCT/US2009/055805, filed Sep. 3, 2009, which claims the benefit of U.S. Provisional Application No. 61/100,983, filed Sep. 29, 2008 and U.S. Provisional Application No. 61/118,759, filed Dec. 1, 2008, each of which is incorporated by reference herein.

Most commercially available therapeutic agents for the treatment of osteoarthritis ("OA") are directed at reducing the inflammation and relieving the pain associated with OA. The approved OA treatments may be invasive, lose efficacy with long term use, and may not be appropriate for treating all patients. New treatment options for patients suffering from OA are desired.

Preclinical studies of estrogens and various selective estrogen receptor modulators (SERMs) have been reported with disease-suppressing activity in models of OA joint disease. Many SERM molecules are known to the artisan. Many of the known SERMs have been found to have estrogen agonist activity in the bone; however, no SERMs are currently approved for treating OA. The selective agonist or antagonistic activity of the SERM molecule on various tissues can modify the safety and efficacy profile of the SERM. For example, SERM molecules having agonist activity at the uterus may be associated with undesirable vaginal bleeding. SERM molecules may have selective agonist and/or antagonist activity for example, in the bone, breast, and/or uterus. Applicants believe that SERM compounds offering potent antagonist activity in the uterus, while having SERM agonist activity in the bone, can be particularly desirable for use in treating OA. SERM compounds having a beneficial effect on OA signs or symptoms while offering an acceptable safety profile would be a particularly useful additional treatment option.

SERM compounds having a [2-(2-Thienyl)-6-hydroxybenzothien-3-yl][4-[2-(1-piperdinyl)ethoxy]phenyl]methanone structure are disclosed in U.S. Pat. No. 5,728,724 ("the '724 patent"). These compounds are disclosed to be useful for the treatment of osteoporosis, postmenopausal syndrome, endometriosis, and various other conditions associated with SERM activity. However, the patent does not teach that these SERM compounds would be useful for treating OA. Additionally, the 724 patent SERM molecules are structurally distinct from the compounds of present invention. In contrast to the '724 patent, the present invention requires a compound having an oxy linker attached to a naphthalene based scaffold.

This invention provides a potent novel SERM compound. Further the SERM molecule provides selective estrogen antagonism at the uterus, providing a particularly desirable pharmacological profile for use in the treatment of OA. Additionally, this selective SERM may provide a desirable safety profile for use in the treatment of OA.

The present invention is directed to a compound of the formula

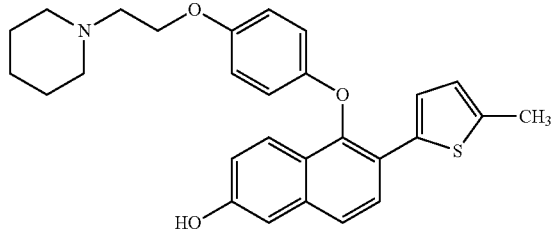 [SMILES: Cc1ccc(-c2ccc3cc(O)ccc3c2Oc2ccc(OCCN3CCCCC3)cc2)s1]

or a pharmaceutically acceptable salt thereof;

In another embodiment, this invention provides compounds of formula I:

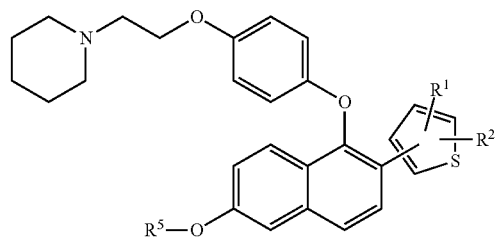

or a pharmaceutically acceptable salt thereof;
wherein
$R^1$ is selected from the group consisting of H, $-C_1-C_4$ alkyl, F, Cl, $-CN$, $-C(O)R^3$, $-(C_1-C_3$ alkyl)OH, $-OCH_3$, $-S(O)_2R^4$, $-S(O)CH_3$, $-CF_3$, and $-S(C_1-C_3$ alkyl);
$R^2$ is selected from the group consisting of H, F, and $CH_3$;
$R^3$ is selected from the group consisting of OH, $-OCH_3$, $-NH(C_0-C_2$ alkyl), $CH_3$, $-N(CH_3)_2$;
$R^4$ is selected from the group consisting of $-C_1-C_4$ alkyl, $-N(CH_3)_2$, and $-CF_3$; and
$R^5$ is selected from the group consisting of H and $CH_3$.

In another embodiment, this invention provides compounds of formula I:

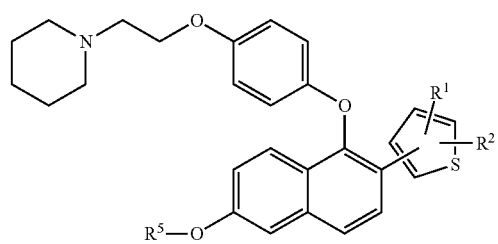

or a pharmaceutically acceptable salt thereof;
wherein
$R^1$ is selected from the group consisting of H, $-C_1-C_4$ alkyl, F, Cl, $-CN$, $-C(O)R^3$, $-(C_1-C_3$ alkyl)OH, $-OCH_3$, $-S(O)_2R^4$, $-S(O)CH_3$, and $-S(C_1-C_3$ alkyl);
$R^2$ is selected from the group consisting of H, F, and $CH_3$;
$R^3$ is selected from the group consisting of OH, $-OCH_3$, $-NH(C_0-C_2$ alkyl), $CH_3$, $-N(CH_3)_2$;
$R^4$ is selected from the group consisting of $C_1-C_4$ alkyl, $-N(CH_3)_2$, and $CF_3$; and
$R^5$ is selected from the group consisting of H and $CH_3$.

In another embodiment, this invention provides compounds of formula I, wherein:

$R^1$ is selected from the group consisting of H, —$C_1$-$C_4$ alkyl, F, Cl, —CN, —C(O)$R^3$, —S(O)$_2R^4$, —S(O)CH$_3$, —SCH$_3$, and —CF$_3$;

$R^2$ is selected from the group consisting of H and CH$_3$;

$R^3$ is selected from the group consisting of CH$_3$, —N(CH$_3$)$_2$,' and —OCH$_3$;

$R^4$ is selected from $C_1$-$C_3$ alkyl; and $R^5$ is selected from the group consisting of H and CH$_3$.

or a pharmaceutically acceptable salt thereof.

In another embodiment, this invention provides compounds of formula I, wherein:

$R^1$ is selected from the group consisting of H, —CH$_3$, —CH$_2$CH$_3$, —CH(CH$_3$)$_2$, —CH$_2$CH(CH$_3$)$_2$, F, Cl, —CN, —C(O)CH$_3$, —C(O)N(CH$_3$)$_2$, —C(O)OCH$_3$, —S(O)$_2$CH(CH$_3$)$_2$, —S(O)$_2$CH$_2$CH$_3$, —S(O)$_2$CH$_3$, —S(O)CH$_3$, —CF$_3$, and —SCH$_3$;

$R^2$ is selected from the group consisting of H and CH$_3$; and $R^5$ is H;

or a pharmaceutically acceptable salt thereof.

In another embodiment, this invention provides compounds of formula I, wherein:

$R^1$ is selected from the group consisting of H, —CH$_3$, —CH$_2$CH$_3$, —CH(CH$_3$)$_2$, —CH$_2$CH(CH$_3$)$_2$, F, Cl, —CN, —C(O)CH$_3$, —C(O)N(CH$_3$)$_2$, —C(O)OCH$_3$, —S(O)$_2$CH(CH$_3$)$_2$, —S(O)$_2$CH$_2$CH$_3$, —S(O)$_2$CH$_3$, —S(O)CH$_3$, —CF$_3$, and —SCH$_3$;

$R^2$ is H; and $R^5$ is H;

or a pharmaceutically acceptable salt thereof.

In another embodiment, this invention provides compounds of formula I, wherein:

$R^1$ is —CH$_3$;

$R^2$ is —CH$_3$; and $R^5$ is H;

or a pharmaceutically acceptable salt thereof.

In another embodiment, this invention provides compounds of formula I that is 2-thiophene:

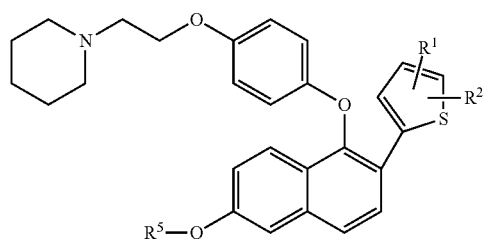

or a pharmaceutically acceptable salt thereof;
wherein $R^1$ is selected from the group consisting of H, —$C_1$-$C_4$ alkyl, F, Cl, —CN, —C(O)$R^3$, —($C_1$-$C_3$ alkyl)OH, —OCH$_3$, —S(O)$_2R^4$, —S(O)CH$_3$, —CF$_3$, and —S($C_1$-$C_3$ alkyl);

$R^2$ is selected from the group consisting of H, F, and CH$_3$;

$R^3$ is selected from the group consisting of OH, —OCH$_3$, —NH($C_0$-$C_2$ alkyl), CH$_3$, —N(CH$_3$)$_2$;

$R^4$ is selected from the group consisting of —$C_1$-$C_4$ alkyl, —N(CH$_3$)$_2$, and —CF$_3$; and $R^5$ is selected from the group consisting of H and CH$_3$.

In another embodiment, this invention provides compounds of formula I that is 3-thiophene:

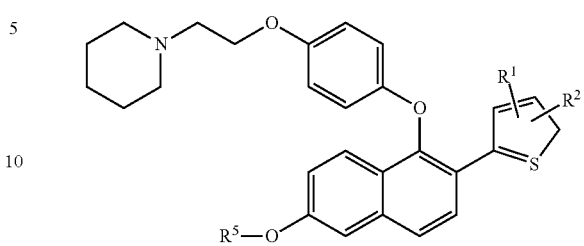

or a pharmaceutically acceptable salt thereof;
wherein $R^1$ is selected from the group consisting of H, —$C_1$-$C_4$ alkyl, F, Cl, —CN, —C(O)$R^3$, —($C_1$-$C_3$ alkyl)OH, —OCH$_3$, —S(O)$_2R^4$, —S(O)CH$_3$, —CF$_3$, and —S($C_1$-$C_3$ alkyl);

$R^2$ is selected from the group consisting of H, F, and CH$_3$;

$R^3$ is selected from the group consisting of OH, —OCH$_3$, —NH($C_0$-$C_2$ alkyl), CH$_3$, —N(CH$_3$)$_2$;

$R^4$ is selected from the group consisting of —$C_1$-$C_4$ alkyl, —N(CH$_3$)$_2$, and —CF$_3$; and $R^5$ is selected from the group consisting of H and CH$_3$.

A further embodiment of this invention provides a method for treating osteoarthritis in a mammal, comprising the step of administering to the mammal a compound as claimed by the present invention.

In another embodiment, the present invention also relates to pharmaceutical compositions comprising a compound of the present invention, or a pharmaceutically acceptable salt, and a pharmaceutically acceptable carrier.

Further, the invention relates to a compound as claimed by the present invention for use as a medicament. Additionally, the present invention relates to a compound as claimed by the present invention for use in the treatment of osteoarthritis, and the use of a compound as claimed by the present invention for the manufacture of a medicament for treating osteoarthritis.

"Pharmaceutically-acceptable salt" refers to salts of the compounds of the invention considered to be acceptable for clinical and/or veterinary use. These salts may be prepared by methods known to the skilled artisan. Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol. 66, No. 1, January 1977. The compounds of the present invention are preferably prepared as pharmaceutical compositions administered by a variety of routes. The term "pharmaceutically acceptable carrier" means that the carrier, diluent, excipients and salt are pharmaceutically compatible with the other ingredients of the composition. Most preferably, these compositions are for oral administration. Pharmaceutically acceptable compositions and processes for preparing same are well known in the art. See, e.g., REMINGTON: THE SCIENCE AND PRACTICE OF PHARMACY (A. Gennaro, et al., eds., 19th ed., Mack Publishing Co., 1995). Preferred pharmaceutically acceptable salts include the hydrochloride, methanesufonate, and methylbenzenesulfonate. The hydrochloride and methylbenzenesulfonate salt are particularly preferred pharmaceutically acceptable salts.

Osteoarthritis (hereinafter "OA") is a chronic degenerative disease affecting the joints. The symptoms of OA are for example, substantial pain, functional limitation, and disability relating to the affected joints.

To date, two studies have investigated the utility of raloxifene, a known SERM, for OA. The first study was a prospective non-placebo controlled observational study in which it was demonstrated that raloxifene use significantly decreased the frequency of reported pain at multiple skeletal sites, decreased the use of analgesics and improved sleep quality. In the second study, raloxifene treatment produced a small but significant improvement in clinical outcome (15% decrease in the WOMAC score) after 1 year of treatment. Both raloxifene and another SERM, levormeloxifene, have also been demonstrated to significantly decrease the urinary levels of CTX-II, a marker of cartilage type II collagen turnover. Novel SERM compounds demonstrating a particular selectivity profile that can be useful for the treatment of OA are desired.

The compounds of the invention can be prepared using the methods illustrated in Scheme A, and as described by the Examples. The preparations and examples are named using ChemDraw Ultra version 10.0 and Symyx® Draw Version 3.1.

The terms and abbreviations used in the Schemes, Preparations, Examples and Procedures herein have their normal meanings unless otherwise designated. For example, as used herein, the following terms have the meanings indicated: "NBS" is N-bromosuccinimide, "BnBr" is benzyl bromide, "$Cs_2CO_3$" is cesium carbonate, "CuOTf" is copper triflate, "$Tf_2O$" is trifluoromethane sulfonic acid anhydride, "Pd(OH)$_2$/C" is Pd(OH)$_2$ on Carbon, "Pd(OAc)$_2$" is palladium (II) acetate, "PCy$_3$" is tricyclohexylphosphine, "ACN" acetonitrile, "CsF" is cesium fluoride, "BBr$_3$" is Boron Tribromide, "DMF" is dimethylformamide, "nBuLi" is n-butyl lithium, "THF" is Tetrahydrofuran, "Et$_3$SiH" is triethylsilane, "TFA" is trifluoroacetic Acid, "POCl$_3$" is phosphoryl chloride, "MgSO$_4$" is magnesium sulfate, "NH$_4$OH" is ammonium hydroxide, "Na$_2$SO$_4$" is sodium sulfate, "Pd(dppf)Cl$_2$" is (1,1'-bis(diphenylphosphino)ferrocene)palladium (II) Chloride, "dppf" is 1,1'-bis(diphenylphosphino)ferrocene, "KOAc" is potassium acetate, "DCM" is dichloromethane, "DIPEA" is diisopropylethylamine, "TFAA" is 2,2,2-trifluoroacetic anhydride, "n-BuLi" is n-butyl lithium, "mCPBA" is meta-chloro-perbenzoic acid, "Pd(PPH$_3$)$_4$" tetrakis(triphenylphosphino)palladium, "TEA" is triethylamine, "DMAC" is N,N-dimethylacetamide, "TBAI" tetra-N-butylammonium iodide, "DMAP" is 4-dimethylaminopyridine, "NaClO$_2$" is sodium chlorite, "DDQ" is 2,3-dichloro-5,6-dicyanobenzoquinone, "DMSO" is dimethyl sulfone, "SCX" is strong cation exchange, "LRMS" is low resolution mass spectrometry, "DSC" is Differential scanning calorimetry, and "MP" is melting point.

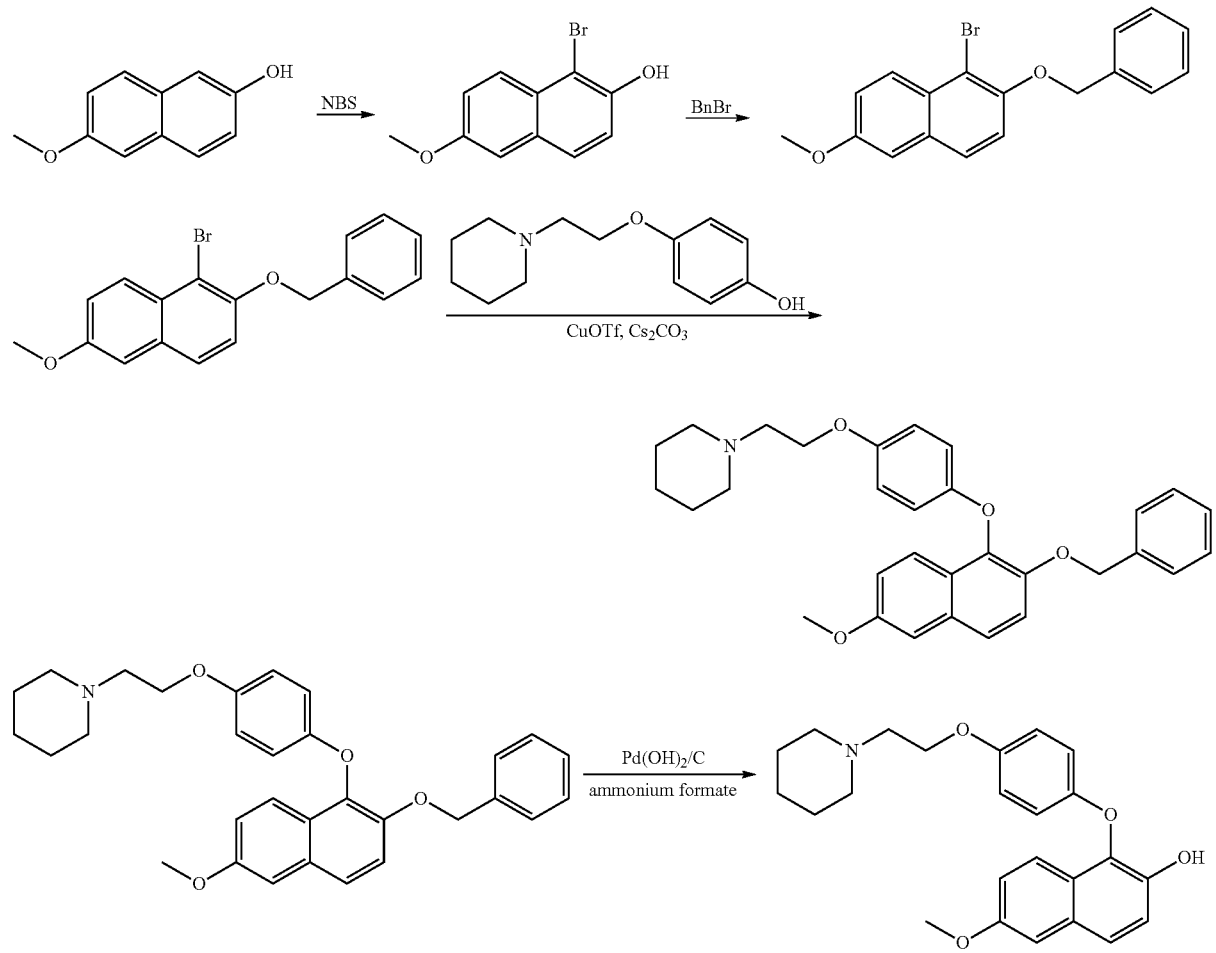

Scheme A

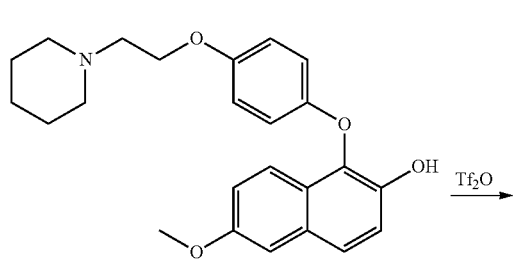
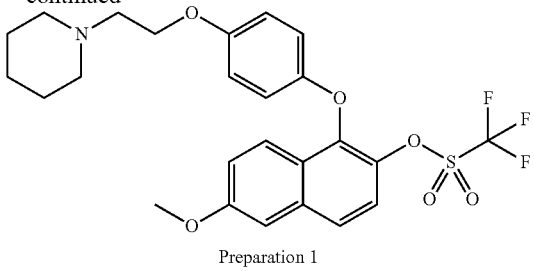
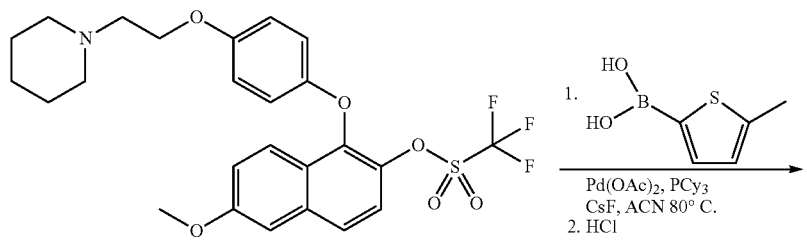
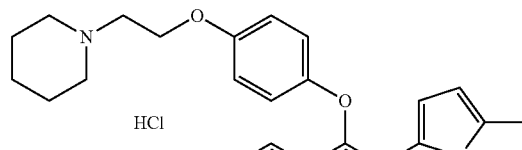
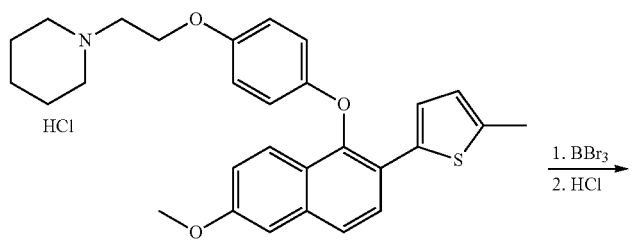
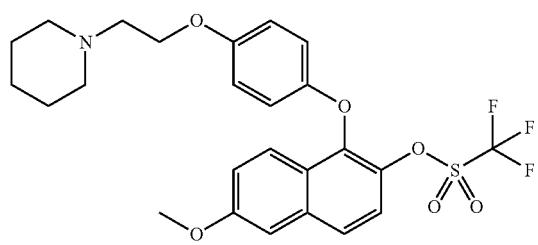 [SMILES: COc1ccc2c(Oc3ccc(OCCN4CCCCC4)cc3)c(OS(=O)(=O)C(F)(F)F)ccc2c1]

Preparation 1

Synthesis of 6-methoxy-1(4-(2-(piperidin-1-yl)ethoxy)phenoxy)naphthalen-2-yl trifluoromethanesulfonate Add 6-methoxynaphthalene-2-ol (20 g, 114.8 mmol) to dimethylformamide (DMF, 250 mL) at ambient temperature followed by N-bromosuccinimide (NBS, 21.5 g, 120 mmol) over a 30 minute period. After 45 minutes, dilute with water (800 mL), collect and dry the precipitate to provide 25.5 g (87%) of 1-bromo-6-methoxy-naphthalen-2-ol.

Add 1-bromo-6-methoxy-naphthalen-2-ol (66.7 g, 264 mmol), potassium carbonate (K₂CO₃, 40.0 g, 290 mmol) and benzyl bromide (49.6 g, 290 mmol) to DMF (800 mL). Stir the mixture at ambient temperature for 1 hour. Add water (400 mL) to precipitate the product. Collect the precipitate and wash the filter cake with heptane (3×125 mL) then dry to provide 2-benzyloxy-1-bromo-6-methoxy-naphthalene (83.7 g, 98.9 mmol).

Combine toluene (200 mL), 2-benzyloxy-1-bromo-6-methoxy-naphthalene (30 g, 87.4 mmol), 4-(2-piperidin-1-yl-ethoxy)phenol (23.2 g, 105 mmol) and cesium carbonate (34.4 g, 105 mmol). Heat the mixture to reflux. Remove a portion of the toluene by distillation (100 mL). Add ethyl acetate (390 mg, 4.37 mmol) and copper triflate benzene complex (2.20 g, 4.37 mmol) to the reaction mixture and stir for 5 minutes. Remove the solvent by distillation and heat the resulting residue to 174° C. for 1.5 hours. Dissolve the residue in a mixture of ethyl acetate (200 mL) and aqueous HCl (1 N, 90 mL). Separate and concentrate the organic solution to a residue. Purify the residue by silica gel chromatography to give 1-{2-[4-(2-benzyloxy-6-methoxy-naphthalen-1-yloxy)-phenoxy]-ethyl}-piperidine (12.4 g, 26.2 mmol).

Add 1-{2-[4-(2-benzyloxy-6-methoxy-naphthalen-1-yloxy)-phenoxy]-ethyl}-piperidine (12.4 g, 25.5 mmol) to a methanol/ethyl acetate mixture (1:1, 490 mL) and heat to form a solution. Remove heat and add ammonium formate (4.83 g, 76.6 mmol) and Pd(OH)₂ on Carbon (20% ww, 1.58 g, 1.12 mmol). Reflux the solution for 50 minutes then filter.

Concentrate the filtrate to provide 6-methoxy-1-[4-(2-piperidin-1-yl-ethoxy)-phenoxy]-naphthalene-2-ol (9.9 g, 25.1 mmol).

Cool dichloromethane (290 mL), triethyamine (3.08 g, 30.4 mmol) and 6-methoxy-1-[4-(2-piperidin-1-yl-ethoxy)-phenoxy]-naphthalene-2-ol (9.2 g, 23.4 g) to −50° C. and add trifluoromethane sulfonic acid anhydride (7.26 g, 25.7 mmol). Stir the resulting mixture at −50° C. for 2 hours then allow the mixture to warm to ambient temperature before stirring for an additional hour. Add brine (150 mL) and separate the organic solution. Wash the organic solution with saturated aqueous NaHCO₃ then dry before concentrating to a residue. Crystallize the residue with ethyl ether-hexanes to provide the title compound (11.2 g, 21.27 mmol). LRMS (m/z): 526 (M+1).

Preparation 2

Synthesis of 1-(2-(4-(6-methoxy-2-(5-methylthiophen-2-yl)naphthalen-1-yloxy)phenoxy)ethyl)piperidine hydrochloride Suspend 6-methoxy-1-(4-(2-(piperidin-1-yl)ethoxy)phenoxy)naphthalen-2-yl trifluoromethanesulfonate (398.8 g; 758.8 mmol), 5-Methyl-2-thiopheneboronic Acid (224 g; 1.58 mol), and cesium fluoride (300 g; 1.97 mol) in acetonitrile (12 L). Degas the resulting suspension via gas inlet tube for 30 minutes while heating to 50° C. Treat the mixture with tricyclohexylphosphine (8 g; 28.5 mmol) and degas for 10 minutes, then treat with palladium (II) acetate (4 g; 17.8 mmol), degas for an additional 5 minutes, and stir overnight at 80° C. Add tricyclohexylphosphine (8 g; 28.5 mmol) and palladium (II) acetate (4 g; 17.8 mmol) and heat the mixture for an additional 8 hours, then allow the solution to slowly cool overnight. Filter the cooled solution through a large glass frit and concentrate the filtrate. Slurry the residue and filter cake in water (4 L) and ethyl acetate (8 L), then transfer to a separatory funnel and treat with saturated aqueous sodium bicarbonate (300 g; 3.57 mol). Stir vigorously for 10 minutes, then separate the layers. Wash the organic layer with saturated aqueous sodium bicarbonate, brine, and dry over MgSO₄ overnight. Filter the mixture, and treat the filtrate with HCl (4N in dioxane, 200 mL, 800 mmol). Stir the resulting slurry 60 minutes; then filter to obtain the title compound (352 g; 690.06 mmol). LRMS (m/z): 474 (M+1-HCl).

EXAMPLE 1

Synthesis of 6-(5-methylthiophen-2-yl)-5-(4-(2-(piperidin-1-yl)ethoxy)phenoxy)naphthalen-2-ol hydrochloride

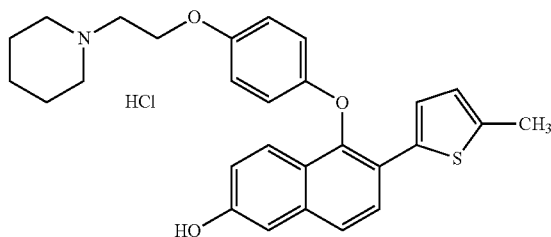 [SMILES: Cc1ccc(-c2ccc3cc(O)ccc3c2Oc2ccc(OCCN3CCCCC3)cc2)s1 ; Cl]

Prepare a solution of 1-(2-(4-(6-methoxy-2-(5-methylthiophen-2-yl)naphthalen-1-yloxy)phenoxy)ethyl)piperidine hydrochloride (346.9 g; 680.07 mmol) in Dichloromethane (12 L) and cool to ~3° C. Treat the resulting solution with Boron Tribromide (1 M in dichloromethane; 301.4 mL 3.19 moles) via cannula over a 20 minute period. Stir the resulting mixture at 0° C. for 90 minutes. Pour the mixture into cracked ice and treat with sodium bicarbonate (1 kg; 11.90 moles) in portions over a 30 minute period. Filter the resulting slurry to provide a dark filter cake. Transfer the filtrate to a separatory funnel Separate the solutions and concentrate the organic solution. Combine the residue with the filter cake and slurry into 20% isopropanol in chloroform (~6 L) and stir with water (4 L) containing 200 g of sodium bicarbonate for 3 hours. Separate the layers and wash the organic layer with brine, dry (MgSO₄), filter and evaporate to afford 324 g of an off-white solid. Purify the resulting solid by silica gel chromatography to obtain 281 g of a pale yellow powder. Stir the solid in Tetrahydrofuran (11 L; 135.18 mol) and treat with S-Triamine (446 g; 2.05 mol). After stirring overnight, filter through Celite and concentrate the filtrate to a white powder. Stir the powder in Tetrahydrofuran (11 L; 135.18 mol) and again treat with S-Triamine (357 g; 1.64 mol). After stirring over the weekend, filter through Celite and concentrate the filtrate to a white powder. Suspend the resulting white solid in methanol (5 L) at room temperature. In a separate container, add HCl (12 N in water, 85 mL, 1.04 mol) in one portion to methanol (2 L). Add this solution to the slurry and stir for 1 hour. Cool the mixture to ~2° C. and stir for 1 hour. Filter the resulting mixture to a cream colored powder. Dry the resulting powder under vacuum at 85° C. overnight to obtain the title compound (258 g, 520.0 mmol). LRMS (m/z): 460 (M+1-HCl). MP (DSC)=248.82° C.

Preparation 66

Synthesis of 6-(5-methylthiophen-2-yl)-5-(4-(2-(piperidin-1-yl)ethoxy)phenoxy)naphthalen-2-ol Dissolve 1-(2-(4-(6-methoxy-2-(5-methylthiophen-2-yl)naphthalen-1-yloxy)phenoxy)ethyl)piperidine hydrochloride (5.15 g, 10.1 mmol) in dichloromethane (340 mL). Cool the resulting solution to 0° C. In a separate container under nitrogen combine neat boron tribromide (3.9 mL, 40.4 mmol) and dichloromethane (36.5 mL). Add the resulting boron tribromide solution to the cooled solution. Stir the resulting mixture at 0° C. for 2.5 hours. Quench the mixture with saturated aqueous sodium bicarbonate and allow it to warm to room temperature. Separate the layers and extract the aqueous layer with 20% methanol in dichloromethane (10 mL×3). Concentrate the combined organic solutions to give a solid. Slurry the solid in methanol (234 mL) and add HCl (1N in water; 10.8 mL). Load the resulting solution onto an SCX acidic ion exchange column. Flush the column with 40% methanol in dichloromethane then elute desired material with 40% 7M ammonia in methanol in dichloromethane. Concentrate the ammonia containing eluent to give the title compound (4.54 g, 9.88 mmol). LRMS (m/z): 460 (M+1).

Preparation 67

Synthesis of 6-(5-methylthiophen-2-yl)-5-(4-(2-(piperidin-1-yl)ethoxy)phenoxy)naphthalen-2-ol methanesulfonate Place 6-(5-methylthiophen-2-yl)-5-(4-(2-(piperidin-1-yl)ethoxy)phenoxy)naphthalen-2-ol (105.7 mg, 0.23 mmol) in a vial. Add ethyl acetate (2 mL) and methanesulfonic acid (18 μL). Warm the resulting mixture to ~60° C. with stirring. Add tetrahydrofuran (1 mL) to the resulting burnt orange solution with some dark brown gum on the bottom of the vial. Sonicate the resulting solution for 15 minutes. Carefully decant the suspension from gum that forms on the flask. Carefully collect the resulting solids by vacuum filtration and wash the resulting cake with pentane (2×2 mL). Dry the resulting solids in a 40° C. vacuum oven overnight to obtain the title compound. MP (DSC)=161.90° C.

Preparation 68

Synthesis of 6-(5-methylthiophen-2-yl)-5-(4-(2-(piperidin-1-yl)ethoxy)phenoxy)naphthalen-2-ol 4-methylbenzenesulfonate Place 6-(5-methylthiophen-2-yl)-5-(4-(2-(piperidin-1-yl)ethoxy)phenoxy)naphthalen-2-ol (103.4 mg, 0.22 mmol) in a vial. Add ethyl acetate (4 mL) and p-toluenesulfonic acid (52 mg, 0.30 mmol) and stir at ~60° C. Add tetrahydrofuran to clarify the solution and sonicate for 15 minutes. Carefully decant the suspension from gum that forms on the flask. Filter the suspension to obtain a cake of very light pink solids. Wash the cake with pentane (2×2 mL) and dry in a 40° C. vacuum oven overnight to obtain the title compound. MP (DSC)= 136.24° C.

Scheme B

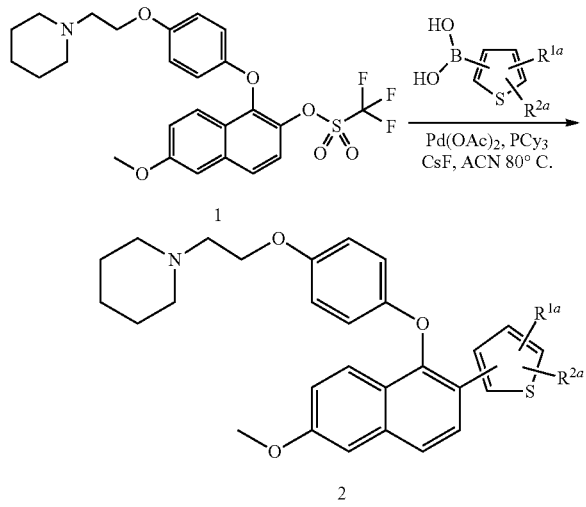

In Scheme B, the optionally substituted thiophene boronic acid is coupled to compounds of formula 1 forming compounds of formula 2 wherein $R^{1a}$ is selected from the group consisting of H, —$C_1$-$C_4$ alkyl, F, Cl, —CN, and —C(O)$R^3$, and $R^{2a}$ is selected from the group consisting of H, F, and $CH_3$. Preferably, $R^{1a}$ is H, —Cl, —C(O)$CH_3$, $CH_3$, CN and $R^{2a}$ is H or $CH_3$.

Preparation 3

1-(2-(4-(6-methoxy-2-(thiophen-2-yl)naphthalen-1-yloxy)phenoxy)ethyl)piperidine

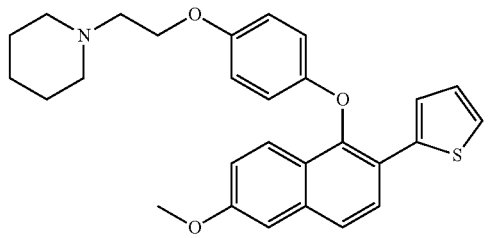 [SMILES: COc1ccc2c(Oc3ccc(OCCN4CCCCC4)cc3)c(-c3cccs3)ccc2c1]

Combine 6-methoxy-1-(4-(2-(piperidin-1-yl)ethoxy)phenoxy)naphthalen-2-yl trifluoromethanesulfonate (6.0 g, 11.4 mmol), Thiophene-2-boronic Acid (4.4 g, 34.3 mmol), tricyclohexylphosphine (1.1 g, 4.0 mmol), palladium (II) acetate (0.51 g, 2.3 mmol), cesium fluoride (15.6 g, 102.8 mmol) and acetonitrile (150 mL; degas with nitrogen for 30 minutes) to a round bottom flask under nitrogen. Warm the resulting mixture to 80° C. and stir for 40 minutes. Filter off solids and wash with acetonitrile. Combine the filtrate and washes and concentrate in vacuo. Dissolve the residue in methanol and load onto an SCX acidic ion exchange column. Flush the column with methanol then elute with 2M ammonia in methanol. Concentrate the ammonia containing eluent in vacuo to give a light brown solid. Purify the solid by silica gel flash chromatography to obtain the title compound (3.88 g, 8.4 mmol). $^1$H NMR ($d_6$-DMSO) δ29 (dd, J=5.9, 11.2 Hz, 2H), 1.43-1.37 (m, 5H), 2.32 (s, 4H), 2.52 (t, J=5.9 Hz, 2H), 3.87 (t, J=6.1 Hz, 2H), 6.62-6.60 (m, 2H), 6.76-6.74 (m, 2H), 7.09-7.03 (m, 2H), 7.37 (d, J=2.6 Hz, 1H), 7.48-7.47 (m, 1H), 7.62-7.59 (m, 2H), 7.76 (d, J=8.8 Hz, 1H), 7.96 (d, J=8.8 Hz, 1H).

The preparations in Table I may be prepared essentially as described in Preparation 3 using the reagent (column 3) listed in place of thiophene-2-boronic Acid.

TABLE I

| Preparation | Structure and Chemical Name | Reagent |
|---|---|---|
| 4 | 1-(2-(4-(2-(5-chlorothiophen-2-yl)-6-methoxynaphthalen-1-yloxy)phenoxy)ethyl)piperidine | 5-chlorothiophen-2-ylboronic acid |

TABLE I-continued

| | | Reagent |
|---|---|---|
| Preparation | Structure and Chemical Name | 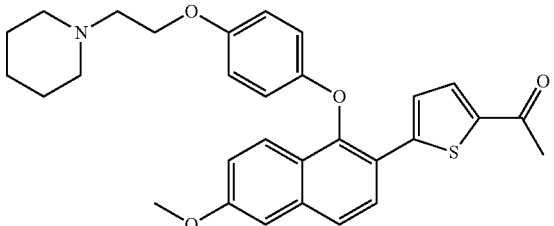 |

| 5 | 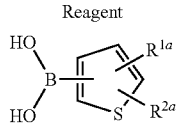<br>1-(5-(6-methoxy-1-(4-(2-(piperidin-1-yl)ethoxy)phenoxy)naphthalen-2-yl)thiophen-2-yl)ethanone | 5-acetylthiophen-2-ylboronic acid |
| 6 | 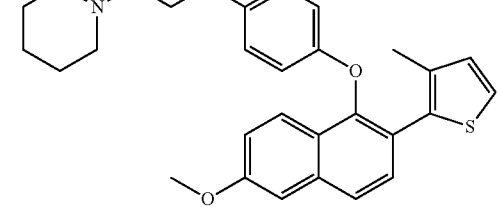<br>1-(2-(4-(6-methoxy-2-(3-methylthiophen-2-yl)naphthalen-1-yloxy)phenoxy)ethyl)piperidine | 3-methylthiophen-2-ylboronic acid |
| 7 | 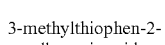<br>1-(4-(6-methoxy-1-(4-(2-(piperidin-1-yl)ethoxy)phenoxy)naphthalen-2-yl)thiophen-2-yl)ethanone | 5-acetylthiophen-3-ylboronic acid |
| 8 | 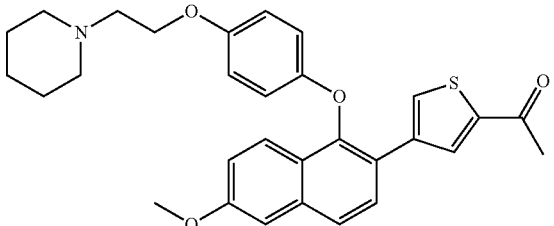<br>1-(2-(4-(6-methoxy-2-(4-methylthiophen-3-yl)naphthalen-1-yloxy)phenoxy)ethyl)piperidine | 4-methylthiophen-3-ylboronic acid |
| 9 | 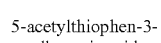<br>1-(2-(4-(2-(3-chlorothiophen-2-yl)-6-methoxynaphthalen-1-yloxy)phenoxy)ethyl)piperidine | 3-chlorothiophen-2-ylboronic acid |

TABLE I-continued

| | | Reagent |
|---|---|---|
| Preparation | Structure and Chemical Name | |

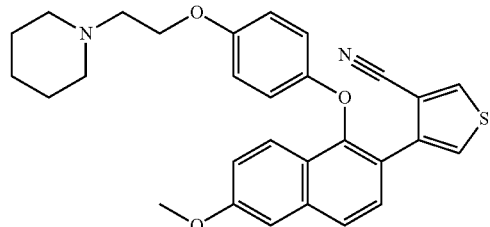

10 — 4-(6-methoxy-1-(4-(2-(piperidin-1-yl)ethoxy)phenoxy)naphthalen-2-yl)thiophene-3-carbonitrile — 3-cyanothiophen-2-ylboronic acid 11 — 1-(2-(4-(2-(2,5-dimethylthiophen-3-yl)-6-methoxynaphthalen-1-yloxy)phenoxy)ethyl)piperidine — 2,5-dimethylthiophen-3-ylboronic acid 12 — 1-(2-(4-(6-methoxy-2-(thiophen-3-yl)naphthalen-1-yloxy)phenoxy)ethyl)piperidine — thiophen-3-ylboronic acid Scheme C

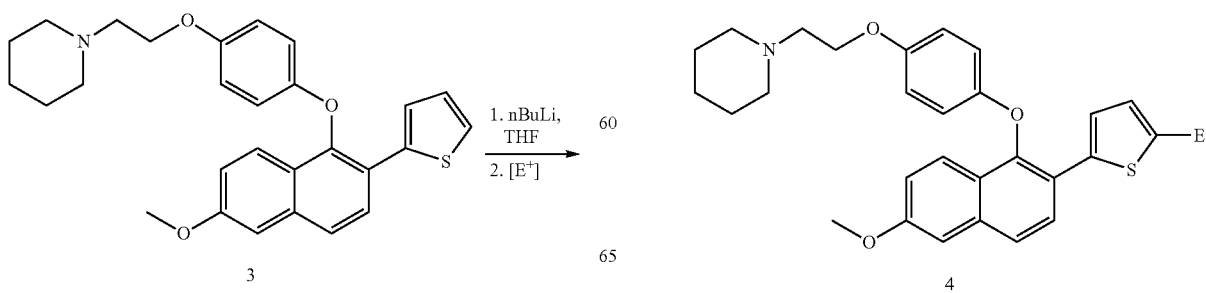

In Scheme C, compounds of formula 3 are first converted to the organo-lithiate and then added to an electrophile ([E⁺]) to form compounds of formula 4 wherein E is —F, —C(O)OH, —S—CH₃, —S—CH(CH₃)₂, —S—CH₂CH₃, —C(O)N(CH₃)₂, —CH₂CH₃, —C(CH₃)₂—OH, or —CH₂CH(CH₃)₂.

Preparation 13

1-(2-(4-(2-(5-fluorothiophen-2-yl)-6-methoxynaphthalen-1-yloxy)phenoxy)ethyl)piperidine

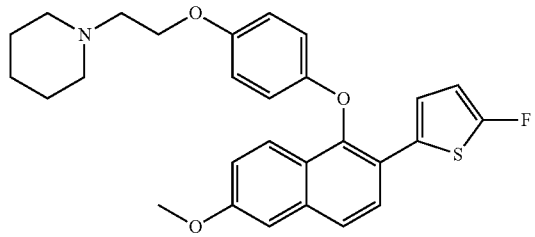 [SMILES: COc1ccc2c(Oc3ccc(OCCN4CCCCC4)cc3)c(-c3ccc(F)s3)ccc2c1]

Add 1-(2-(4-(6-methoxy-2-(thiophen-2-yl)naphthalen-1-yloxy)phenoxy)ethyl)piperidine (153 mg, 0.4 mmol) and tetrahydrofuran (3.3 mL) to a screw-cap vial under argon. Cool the resulting solution to −78° C. Add n-butyl lithium (1.6M in hexanes; 230 μL, 0.4 mmol) dropwise. Warm the resulting solution to 0° C. and stir for 30 min. Add a solution of N-fluorobenzenesulfonimide (210.0 mg; 0.6 mmol) in tetrahydrofuran (500 μL). Allow the resulting mixture to warm to room temperature and stir for 2 hours. Add 1M HCl, dilute with ether and pass through an SCX acidic ion exchange column. Flush the column with methanol then elute desired material with 2M ammonia in methanol. Concentrate the ammonia containing eluent to give a yellow solid. Purify the yellow solid on a silica gel flash chromatography to obtain the title compound (59.0 mg, 0.1 mmol): mass spectrum (m/z): 478 (M+1).

The preparations in Table II may be prepared essentially as described in Preparation 13 using the reagent (column 3) listed in place of N-fluorobenzenesulfonimide.

TABLE II

| Preparation | Chemical Name | Reagent [E+] |
|---|---|---|
| 14 | 5-(6-methoxy-1-(4-(2-(piperidin-1-yl)ethoxy)phenoxy)naphthalen-2-yl)thiophene-2-carboxylic acid | Carbondioxide |
| 15 | 1-(2-(4-(6-methoxy-2-(5-(methylthio)thiophen-2-yl)naphthalen-1-yloxy)phenoxy)ethyl)piperidine | Dimethyldisulfide |
| 16 | 1-(2-(4-(2-(5-(isopropylthio)thiophen-2-yl)-6-methoxynaphthalen-1-yloxy)phenoxy)ethyl)piperidine | Diisopropyldisulfide |

TABLE II-continued

| Preparation | Chemical Name | Reagent [E+] |
|---|---|---|
| 17 | 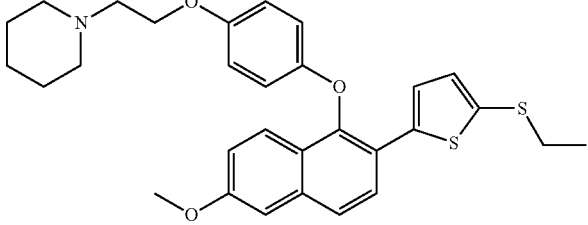 1-(2-(4-(2-(5-(ethylthio)thiophen-2-yl)-6-methoxynaphthalen-1-yloxy)phenoxy)ethyl)piperidine | Diethyldisulfide |
| 18 | 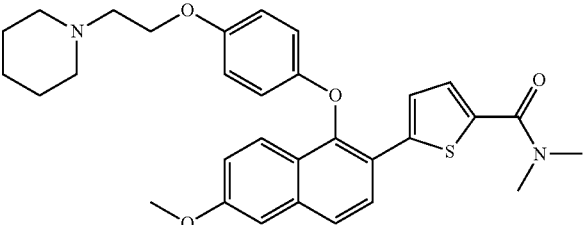 5-(6-methoxy-1-(4-(2-(piperidin-1-yl)ethoxy)phenoxy)naphthalen-2-yl)-N,N-dimethylthiophene-2-carboxamide | N,N-dimethylchloroformamide |
| 19 | 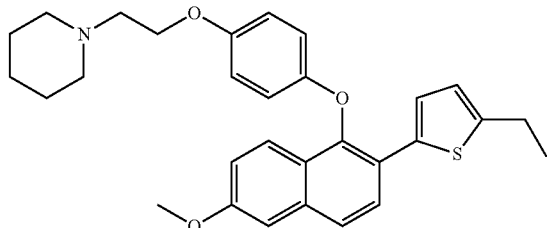 1-(2-(4-(2-(5-ethylthiophen-2-yl)-6-methoxynaphthalen-1-yloxy)phenoxy)ethyl)piperidine | Iodoethane |
| 20 | 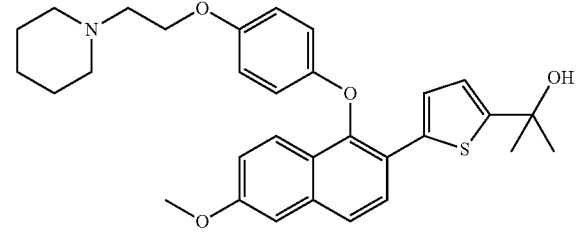 2-(5-(6-methoxy-1-(4-(2-(piperidin-1-yl)ethoxy)phenoxy)naphthalen-2-yl)thiophen-2-yl)propan-2-ol | Acetone |
| 21 | 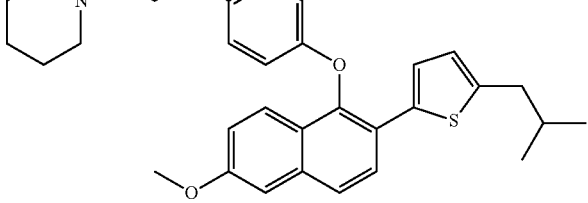 1-(2-(4-(2-(5-isobutylthiophen-2-yl)-6-methoxynaphthalen-1-yloxy)phenoxy)ethyl)piperidine | 1-Iodo-2-methylpropane |

Scheme D

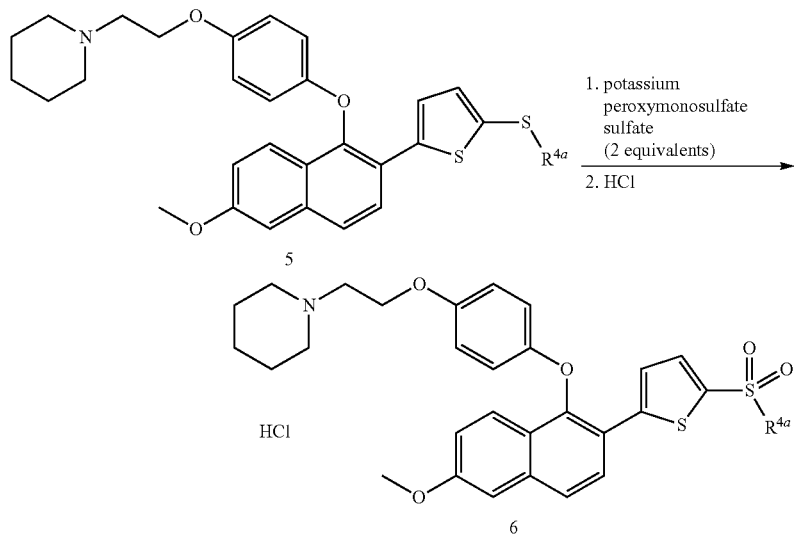

In Scheme D, compounds of formula 5 are oxidized with two equivalents of potassium peroxymonosulfate sulfate to form the compounds of formula 6 wherein $R^{4a}$ is —$CH_3$, —$CH_2CH_3$, or —$CH(CH_3)_2$.

Preparation 22

1-(2-(4-(2-(5-(ethylsulfonyl)thiophen-2-yl)-6-methoxynaphthalen-1-yloxy)phenoxy)ethyl)piperidine hydrochloride

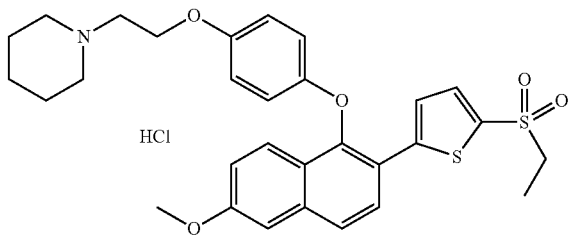 [SMILES: CCS(=O)(=O)c1ccc(-c2ccc3cc(OC)ccc3c2Oc2ccc(OCCN3CCCCC3)cc2)s1 ; Cl]

Add 1-(2-(4-(2-(5-(ethylthio)thiophen-2-yl)-6-methoxynaphthalen-1-yloxy)phenoxy)ethyl)piperidine (226 mg, 0.43 mmol), tetrahydrofuran (8.7 mL) and methanol (8.7 mL) to a round bottom flask under nitrogen. Cool the resulting solution to 0° C. and add a solution of potassium peroxymonosulfate sulfate (535 mg. 0.87 mmol) in water (4.5 mL). Stir the resulting mixture at 0° C. for 30 min. Allow the mixture to warm to room temperature and stir for 1 hour. Load the mixture onto an SCX acidic ion exchange column. Flush column with a 1:1 mixture of methanol and dichloromethane then elute with a 1:1 mixture of 2M ammonia in methanol and dichloromethane. Concentrate the ammonia containing eluent in vacuo to give an off white foam. Dissolve the foam in dichloromethane and treat with HCl (1M in ether; 900 uL). Concentrate the resulting mixture in vacuo to obtain the title compound (142 mg, 0.24 mmol): mass spectrum (m/z): 552 (M+1-HCl).

The preparations in Table III may be prepared essentially as described in Preparation 22 using the reagent (column 3) listed in place of 1-(2-(4-(2-(5-(ethylthio)thiophen-2-yl)-6-methoxynaphthalen-1-yloxy)phenoxy)ethyl)piperidine.

TABLE III

| Preparation | Chemical Name | Preparation used as the reagent |
|---|---|---|
| 23 | 1-(2-(4-(6-methoxy-2-(5-(methylsulfonyl)thiophen-2-yl)naphthalen-1-yloxy)phenoxy)ethyl)piperidine hydrochloride | 15 |

TABLE III-continued

| Preparation | Chemical Name | Preparation used as the reagent |
|---|---|---|
| 24 | 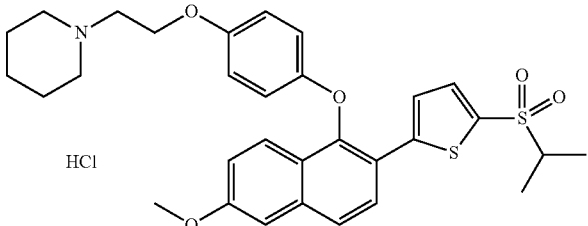<br>1-(2-(4-(2-(5-(isopropylsulfonyl)thiophen-2-yl)-6-methoxynaphthalen-1-yloxy)phenoxy)ethyl)piperidine hydrochloride | 16 |

Scheme E

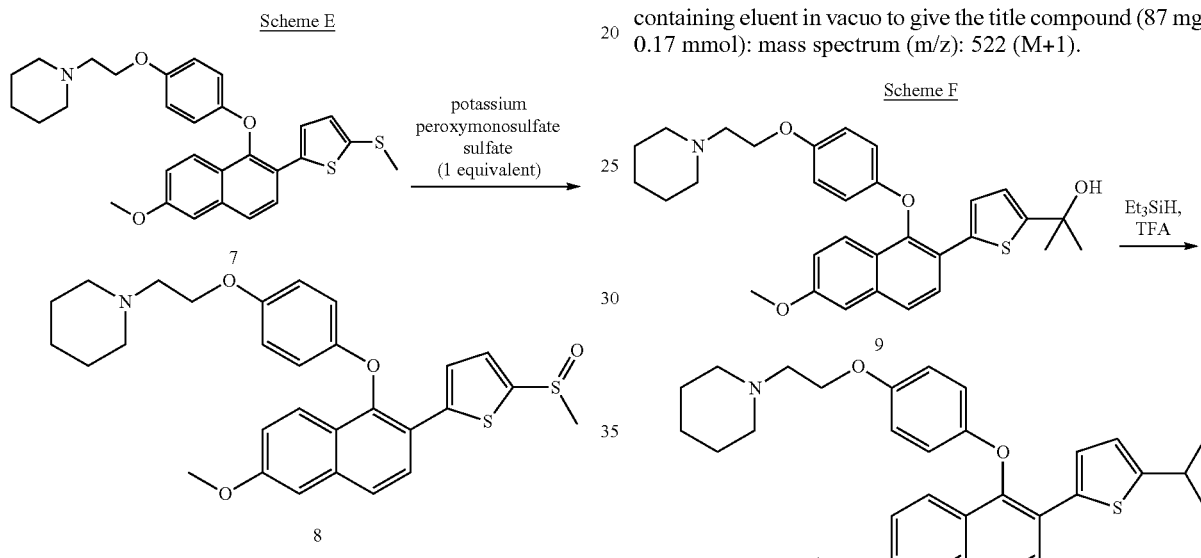

In Scheme E, the compound of formula 7 is oxidized with one equivalent of potassium peroxymonosulfate sulfate to form the compound of formula 8.

Preparation 25

1-(2-(4-(6-methoxy-2-(5-(methylsulfinyl)thiophen-2-yl)naphthalen-1-yloxy)phenoxy)ethyl)piperidine

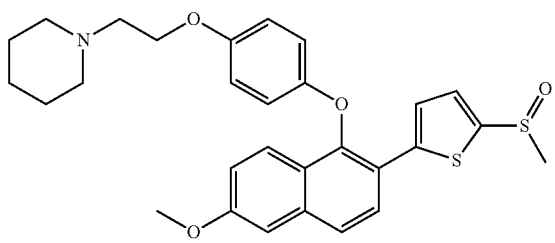 [SMILES: COc1ccc2c(Oc3ccc(OCCN4CCCCC4)cc3)c(-c3ccc(S(C)=O)s3)ccc2c1]

Add 1-(2-(4-(6-methoxy-2-(5-(methylthio)thiophen-2-yl)naphthalen-1-yloxy)phenoxy)ethyl)piperidine (84 mg, 0.17 mmol), tetrahydrofuran (3.3 mL) and methanol (3.3 mL) to a round bottom flask under nitrogen. Cool the resulting solution to 0° C. and add solution of potassium peroxymonosulfate sulfate (102 mg; 0.17 mmol) in water (1.7 mL). Stir the resulting mixture at 0° C. for 30 min. Load the mixture onto an SCX acidic ion exchange column. Flush the column with 1:1 methanol/dichloromethane and elute with 1:1 2M ammonia in methanol/dichloromethane. Concentrate the ammonia containing eluent in vacuo to give the title compound (87 mg, 0.17 mmol): mass spectrum (m/z): 522 (M+1).

Scheme F

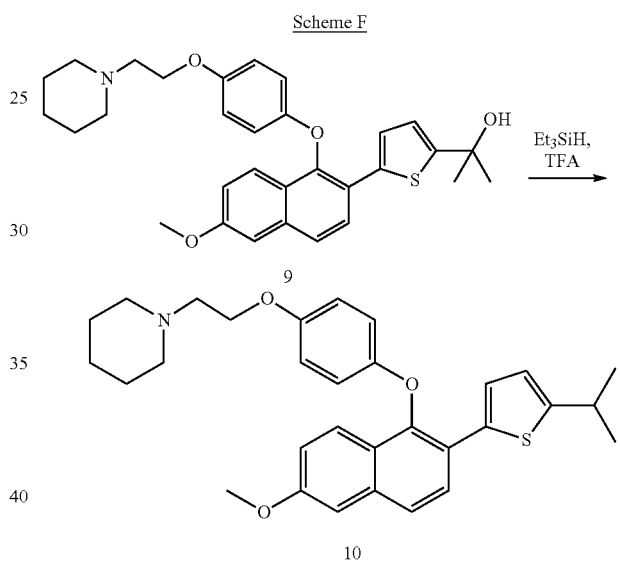

In Scheme F, the compounds of formula 9 are reduced to the compound of formula 10.

Preparation 26

1-(2-(4-(2-(5-isopropylthiophen-2-yl)-6-methoxynaphthalen-1-yloxy)phenoxy)ethyl)piperidine

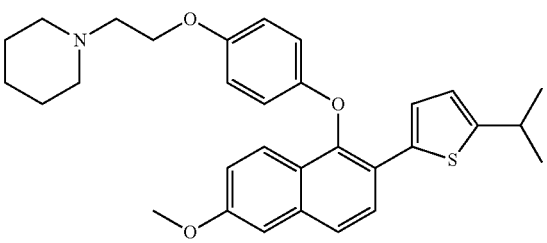 [SMILES: COc1ccc2c(Oc3ccc(OCCN4CCCCC4)cc3)c(-c3ccc(C(C)C)s3)ccc2c1]

Add 2-(5-(6-methoxy-1-(4-(2-(piperidin-1-yl)ethoxy)phenoxy)naphthalen-2-yl)thiophen-2-yl)propan-2-ol (84 mg; 0.16 mmol), triethylsilane (1.7 mL) and dichloromethane (0.85 mL) to a flask under argon. Add trifluoroacetic acid (0.81 mL) and stir the resulting mixture for 45 minutes. Load the mixture onto an SCX acidic ion exchange column. Flush the column with 1:2 methanol/dichloromethane and elute with 1:2 2M ammonia in methanol/dichloromethane. Concentrate the ammonia containing eluent in vacuo to give the title compound (73.1 mg; 0.15 mmol): Mass spectrum (m/z): 502 (M+1).

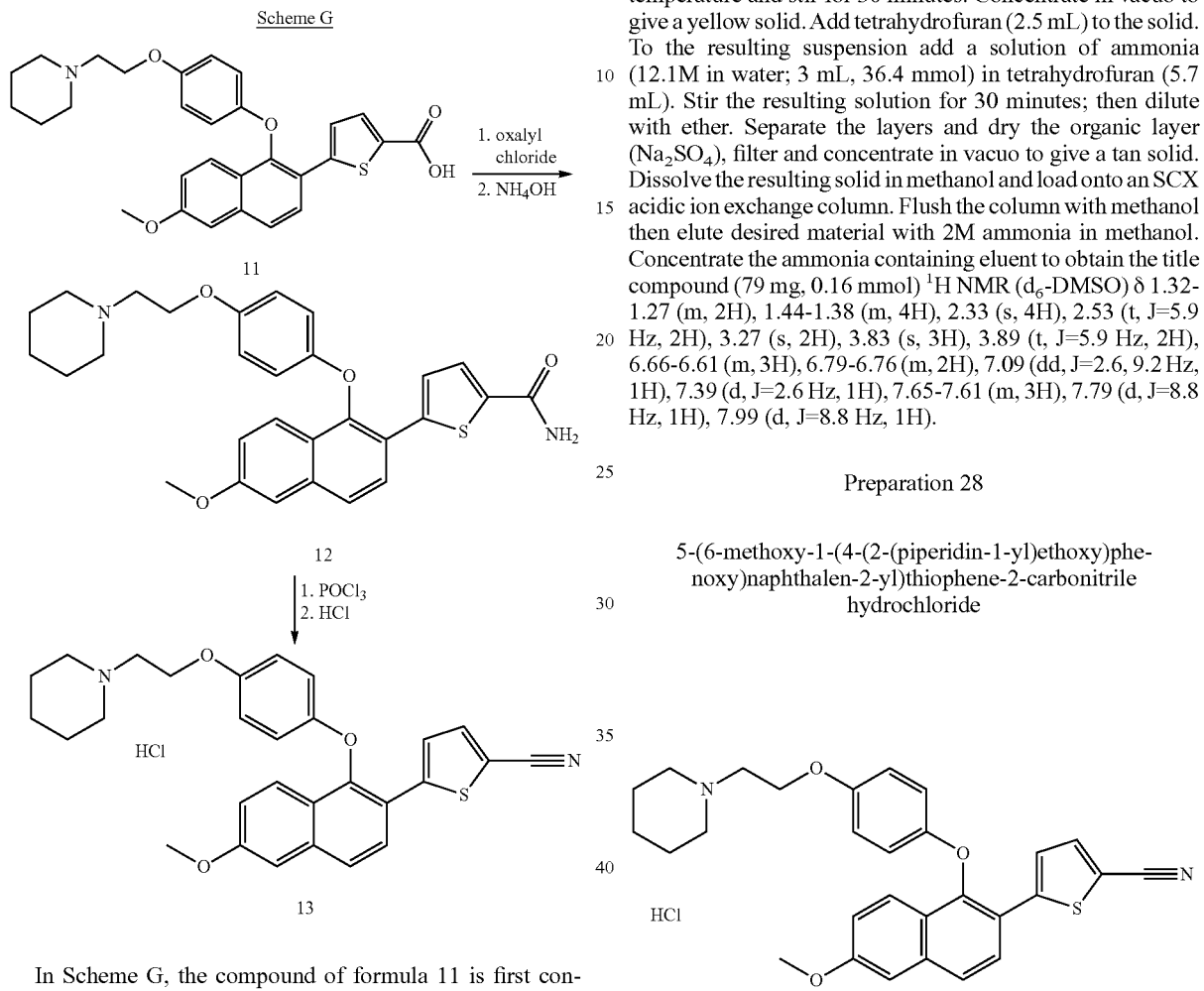

Scheme G

In Scheme G, the compound of formula 11 is first converted to the acid chloride and then subjected to ammonium hydroxide to form the amide of the compound of formula 12. The compound of formula 12 is then dehydrated and then the hydrochloride salt is formed to provide the compound of formula 13.

Preparation 27

5-(6-methoxy-1-(4-(2-(piperidin-1-yl)ethoxy)phenoxy)naphthalen-2-yl)thiophene-2-carboxamide

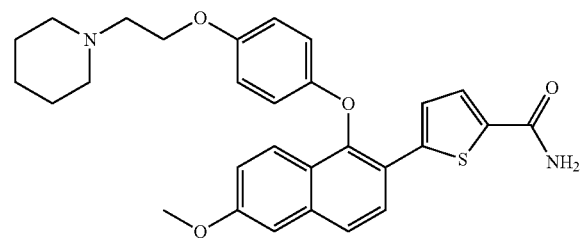 [SMILES: COc1ccc2c(Oc3ccc(OCCN4CCCCC4)cc3)c(-c3ccc(C(N)=O)s3)ccc2c1]

Add 5-(6-methoxy-1-(4-(2-(piperidin-1-yl)ethoxy)phenoxy)naphthalene-2-yl)thiophene-2-carboxylic acid (86 mg, 0.2 mmol) and dichloromethane (2.4 mL) to a round bottom flask under nitrogen. Cool the suspension to 0° C. and add sequentially oxalyl chloride (22.2 μL, 0.3 mmol) and dimethylformamide (30.0 μL). Warm the resulting mixture to room temperature and stir for 30 minutes. Concentrate in vacuo to give a yellow solid. Add tetrahydrofuran (2.5 mL) to the solid. To the resulting suspension add a solution of ammonia (12.1M in water; 3 mL, 36.4 mmol) in tetrahydrofuran (5.7 mL). Stir the resulting solution for 30 minutes; then dilute with ether. Separate the layers and dry the organic layer ($Na_2SO_4$), filter and concentrate in vacuo to give a tan solid. Dissolve the resulting solid in methanol and load onto an SCX acidic ion exchange column. Flush the column with methanol then elute desired material with 2M ammonia in methanol. Concentrate the ammonia containing eluent to obtain the title compound (79 mg, 0.16 mmol) $^1$H NMR ($d_6$-DMSO) δ 1.32-1.27 (m, 2H), 1.44-1.38 (m, 4H), 2.33 (s, 4H), 2.53 (t, J=5.9 Hz, 2H), 3.27 (s, 2H), 3.83 (s, 3H), 3.89 (t, J=5.9 Hz, 2H), 6.66-6.61 (m, 3H), 6.79-6.76 (m, 2H), 7.09 (dd, J=2.6, 9.2 Hz, 1H), 7.39 (d, J=2.6 Hz, 1H), 7.65-7.61 (m, 3H), 7.79 (d, J=8.8 Hz, 1H), 7.99 (d, J=8.8 Hz, 1H).

Preparation 28

5-(6-methoxy-1-(4-(2-(piperidin-1-yl)ethoxy)phenoxy)naphthalen-2-yl)thiophene-2-carbonitrile hydrochloride

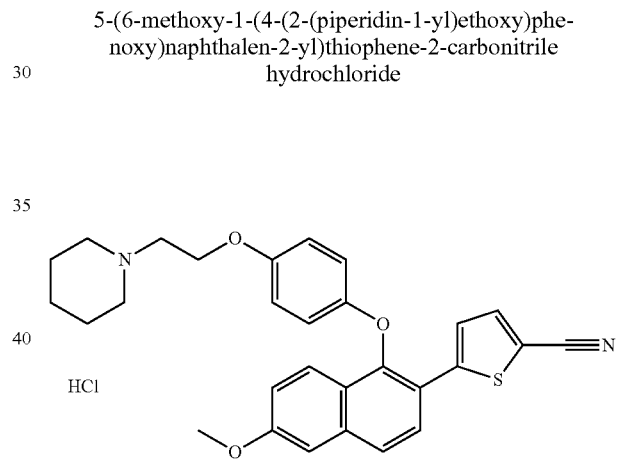

Add 5-(6-methoxy-1-(4-(2-(piperidin-1-yl)ethoxy)phenoxy)naphthalen-2-yl)thiophene-2-carboxamide (79 mg, 0.16 mmol) and phosphoryl chloride (13 mL, 139.9 mmol) to a round bottom flask under nitrogen. Warm the resulting mixture to 100° C. and stir for 15 min. Cool the mixture to room temperature and concentrate in vacuo to give a yellow residue. Carefully quench the resulting residue with methanol and load onto an SCX acidic ion exchange column. Flush the column with methanol then elute desired material with 2M ammonia in methanol. Concentrate the ammonia containing eluent in vacuo to give a pale yellow solid. Dissolve the resulting solid in dichloromethane and treat with HCl (1M in ether, 5 mL). Concentrate in vacuo to obtain the title compound (81.5 mg, 0.16 mmol) $^1$H NMR ($d_6$-DMSO) δ 0.82-0.73 (m, 1H), 1.33-1.23 (m, 4H), 2.88-2.80 (m, 2H), 3.36-3.31 (m, 5H), 3.81 (s, 3H), 4.23-4.19 (m, 2H), 6.73-6.63 (m, 2H), 6.87-6.77 (m, 2H), 7.15-7.09 (m, 1H), 7.41-7.36 (m, 1H), 7.62-7.54 (m, 1H), 7.87-7.77 (m, 3H), 8.09-8.05 (m, 1H), 10.58-10.45 (m, 1H).

Scheme H

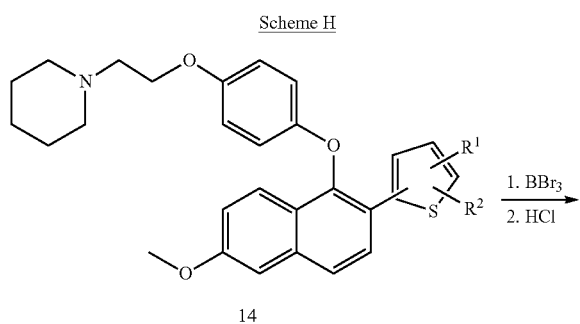

The compounds of formula 14 are deprotected to form a hydrochloride salt of compounds of formula I.

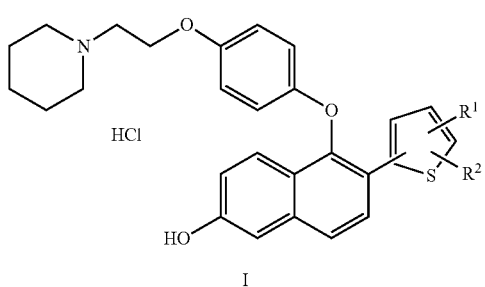

EXAMPLE 5

5-(4-(2-(piperidin-1-yl)ethoxy)phenoxy)-6-(thiophen-2-yl)naphthalen-2-ol hydrochloride Dissolve 1-(2-(4-(6-methoxy-2-(thiophen-2-yl)naphthalen-1-yloxy)phenoxy)ethyl)piperidine (100 mg, 0.22 mmol) in dichloromethane and treat with HCl (1M in ether; 220 μL, 0.22 mmol). Concentrate in vacuo to give a yellow solid and add dichloromethane (7.3 mL). Cool the resulting solution to 0° C. and add boron tribromide (1M in dichloromethane; 870 μL, 0.87 mmol). Stir the resulting mixture at 0° C. for 2.5 hours. Quench the mixture with saturated aqueous sodium bicarbonate and allow to warm to room temperature. Separate the layers and extract the aqueous layer with 20% methanol in dichloromethane (10 mL×3). Dry combined organic layers ($Na_2SO_4$), filter and concentrate in vacuo to give a yellow residue. Purify the residue by silica gel flash chromatography to give an off-white foam. Suspend the foam in ACN and add HCL (5M in water; 1 mL). Freeze the resulting solution and lyophilize to obtain the title compound (50.5 mg, 0.12 mmol): mass spectrum (m/z): 446 (M+1-HCl).

The Examples in Table IV may be prepared essentially by the deprotection procedure as described in Example 5.

TABLE IV

| Example | Preparation used in the deprotection procedure | Structure and Chemical Name | Mass Spectrum (m/z) |
|---|---|---|---|
| 6 | 19 | 6-(5-ethylthiophen-2-yl)-5-(4-(2-(piperidin-1-yl)ethoxy)phenoxy)naphthalen-2-ol hydrochloride | 474 (M + 1 − HCl) |
| 7 | 26 | 6-(5-isopropylthiophen-2-yl)-5-(4-(2-(piperidin-1-yl)ethoxy)phenoxy)naphthalen-2-ol hydrochloride | 488 (M + 1 − HCl) |

TABLE IV-continued

| Example | Preparation used in the deprotection procedure | Structure and Chemical Name | Mass Spectrum (m/z) |
|---|---|---|---|
| 8 | 21 | 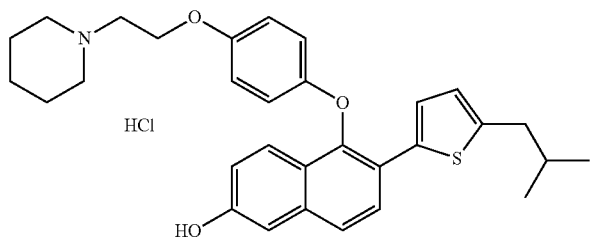<br>6-(5-isobutylthiophen-2-yl)-5-(4-(2-(piperidin-1-yl)ethoxy)phenoxy)naphthalen-2-ol hydrochloride | 502 (M + 1 − HCl) |
| 9 | 6 | 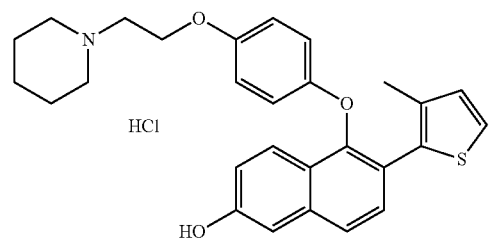<br>6-(3-methylthiophen-2-yl)-5-(4-(2-(piperidin-1-yl)ethoxy)phenoxy)naphthalen-2-ol hydrochloride | 460 (M + 1 − HCl) |
| 10 | 7 | 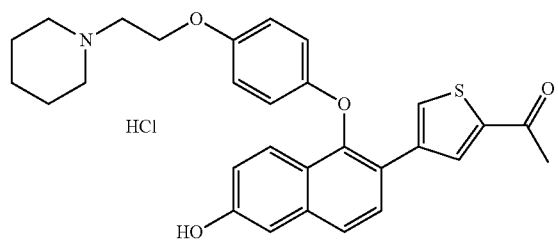<br>1-(4-(6-hydroxy-1-(4-(2-(piperidin-1-yl)ethoxy)phenoxy)naphthalen-2-yl)thiophen-2-yl)ethanone hydrochloride | 488 (M + 1 − HCl) |
| 11 | 8 | 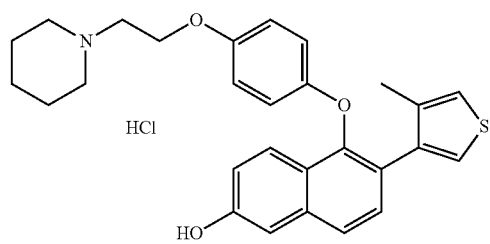<br>6-(4-methylthiophen-3-yl)-5-(4-(2-(piperidin-1-yl)ethoxy)phenoxy)naphthalen-2-ol hydrochloride | 460 (M + 1 − HCl) |
| 12 | 9 | 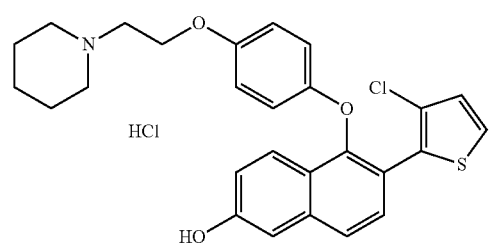<br>6-(3-chlorothiophen-2-yl)-5-(4-(2-(piperidin-1-yl)ethoxy)phenoxy)naphthalen-2-ol hydrochloride | 480 (M + 1 − HCl) |

TABLE IV-continued

| Example | Preparation used in the deprotection procedure | Structure and Chemical Name | Mass Spectrum (m/z) |
|---|---|---|---|
| 13 | 25 | 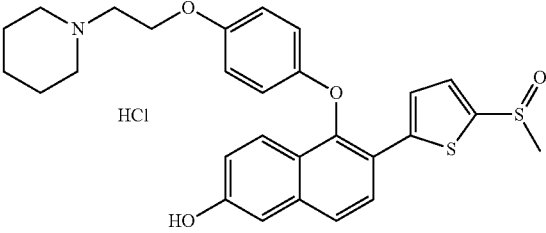<br>6-(5-(methylsulfinyl)thiophen-2-yl)-5-(4-(2-(piperidin-1-yl)ethoxy)phenoxy)naphthalen-2-ol hydrochloride | 508<br>(M + 1 − HCl) |
| 14 | 10 | 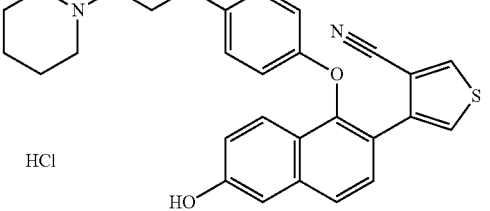<br>4-(6-hydroxy-1-(4-(2-(piperidin-1-yl)ethoxy)phenoxy)naphthalen-2-yl)thiophene-3-carbonitrile hydrochloride | 471<br>(M + 1 − HCl) |
| 15 | 11 | 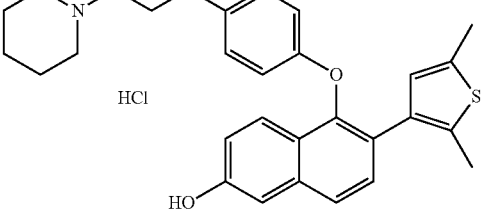<br>6-(2,5-dimethylthiophen-3-yl)-5-(4-(2-(piperidin-1-yl)ethoxy)phenoxy)naphthalen-2-ol hydrochloride | 474<br>(M + 1 − HCl) |
| 16 | 24 | 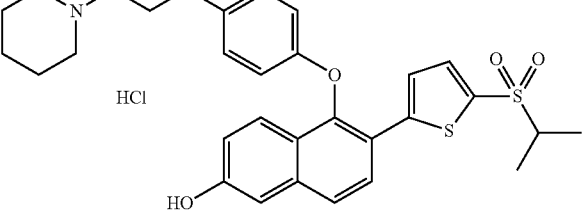<br>6-(5-(isopropylsulfonyl)thiophen-2-yl)-5-(4-(2-(piperidin-1-yl)ethoxy)phenoxy)naphthalen-2-ol hydrochloride | 552<br>(M + 1 − HCl) |
| 17 | 22 | 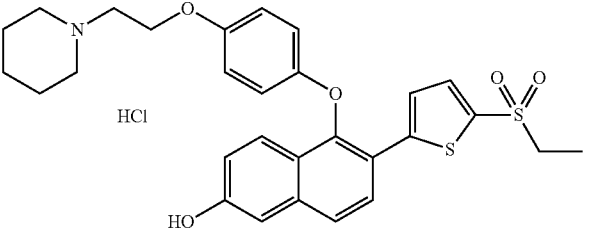<br>6-(5-(ethylsulfonyl)thiophen-2-yl)-5-(4-(2-(piperidin-1-yl)ethoxy)phenoxy)naphthalen-2-ol hydrochloride | 538<br>(M + 1 − HCl) |

TABLE IV-continued

| Example | Preparation used in the deprotection procedure | Structure and Chemical Name | Mass Spectrum (m/z) |
|---|---|---|---|
| 18 | 15 | 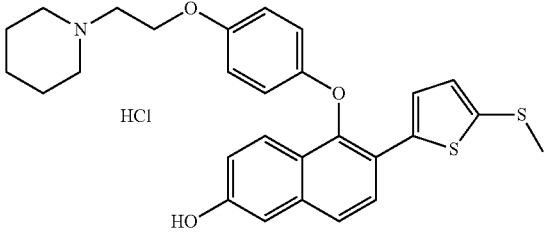  6-(5-(methylthio)thiophen-2-yl)-5-(4-(2-(piperidin-1-yl)ethoxy)phenoxy)naphthalen-2-ol hydrochloride | 492 (M + 1 − HCl) |
| 19 | 18 | 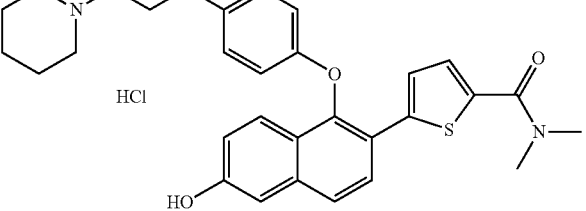  5-(6-hydroxy-1-(4-(2-(piperidin-1-yl)ethoxy)phenoxy)naphthalen-2-yl)-N,N-dimethylthiophene-2-carboxamide hydrochloride | 517 (M + 1 − HCl). |
| 20 | 5 | 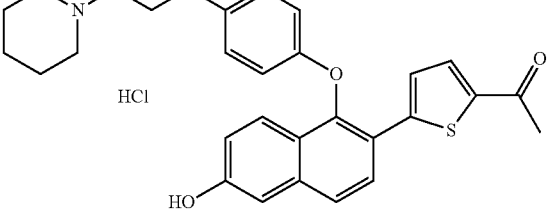  1-(2-(6-hydroxy-1-(4-(2-(piperidin-1-yl)ethoxy)phenoxy)naphthalen-2-yl)thiophen-3-yl)ethanone hydrochloride | 488 (M + 1 − HCl) |
| 21 | 13 | 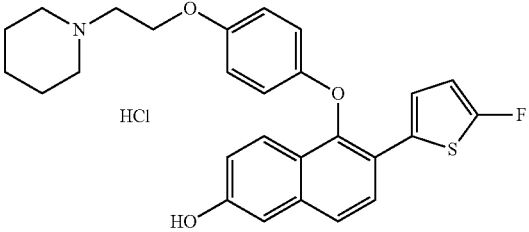  6-(5-fluorothiophen-2-yl)-5-(4-(2-(piperidin-1-yl)ethoxy)phenoxy)naphthalen-2-ol hydrochloride | 464 (M + 1 − HCl). |
| 22 | 23 | 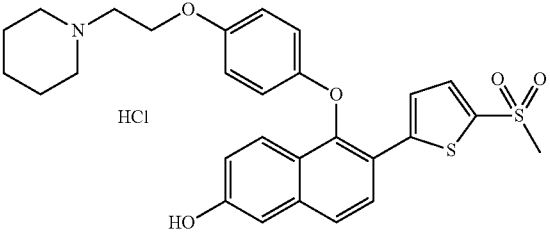  6-(5-(methylsulfonyl)thiophen-2-yl)-5-(4-(2-(piperidin-1-yl)ethoxy)phenoxy)naphthalen-2-ol hydrochloride | 524 (M + 1 − HCl). |

TABLE IV-continued

| Example | Preparation used in the deprotection procedure | Structure and Chemical Name | Mass Spectrum (m/z) |
|---|---|---|---|
| 23 | 28 | 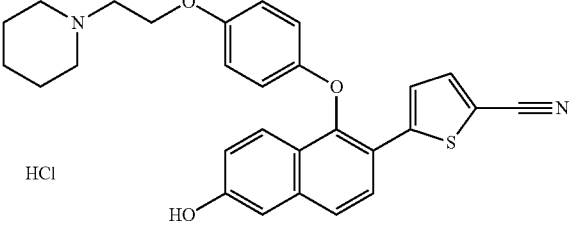<br>5-(6-hydroxy-1-(4-(2-(piperidin-1-yl)ethoxy)phenoxy)naphthalen-2-yl)thiophene-2-carbonitrile hydrochloride | 471 (M + 1 − HCl). |
| 24 | 4 | 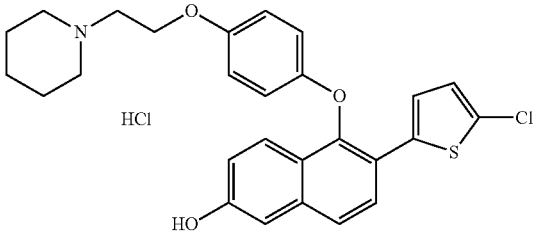<br>6-(5-chlorothiophen-2-yl)-5-(4-(2-(piperidin-1-yl)ethoxy)phenoxy)naphthalen-2-ol hydrochloride | 480 (M + 1 − HCl). |
| 25 | 12 | 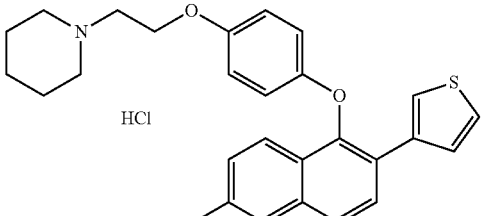<br>5-(4-(2-(piperidin-1-yl)ethoxy)phenoxy)-6-(thiophen-3-yl)naphthalen-2-ol hydrochloride | 446 (M + 1 − HCl) |

Scheme I

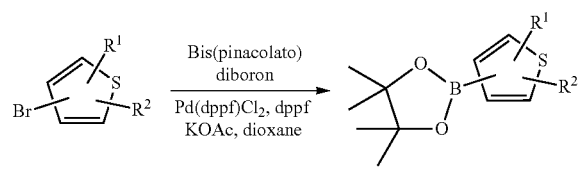

Preparation 29

4,4,5,5-tetramethyl-2-(4-methylthiophen-3-yl)-1,3,2-dioxaborolane

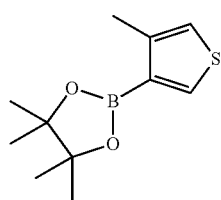

Add 3-Bromo-4-methylthiophene (0.885 g, 5.00 mmol), (1,1'-Bis(diphenylphosphino)ferrocene)palladium(II) Chloride (408 mg, 499.82 μmol), 1,1'-Bis(diphenylphosphino)ferrocene (277.09 mg, 499.82 μmol), Bis(pinacolato)diboron (2.54 g, 10 mmol), Potassium Acetate (1.47 g, 14.99 mmol) and 1,4-Dioxane (50 mL) to a round bottom flask. Purge the reaction vessel with argon. Stir the mixture at 85° C. for 16 hours. Cool the mixture to room temperature. Filter mixture and wash the solids with 1,4-dioxane. Concentrate the filtrate. Purify the resulting residue by flash chromatography on silica to obtain the title compound (0.62 g, 2.5 mmol).

The preparations in Table V may be prepared essentially as described in Preparation 29 using the reagent (column 3) listed in place of 3-bromo-4-methylthiophene.

TABLE V

| Preparation | Structure and Chemical Name | Reagent |
|---|---|---|
| 30 | 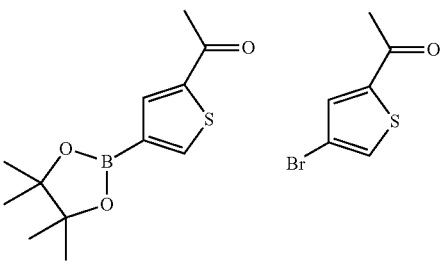<br>1-(4-(4,4,5,5-tetramethyl-1,3,2-dioxaborolan-2-yl)thiophen-2-yl)ethanone | 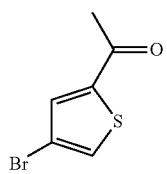 |

Scheme J

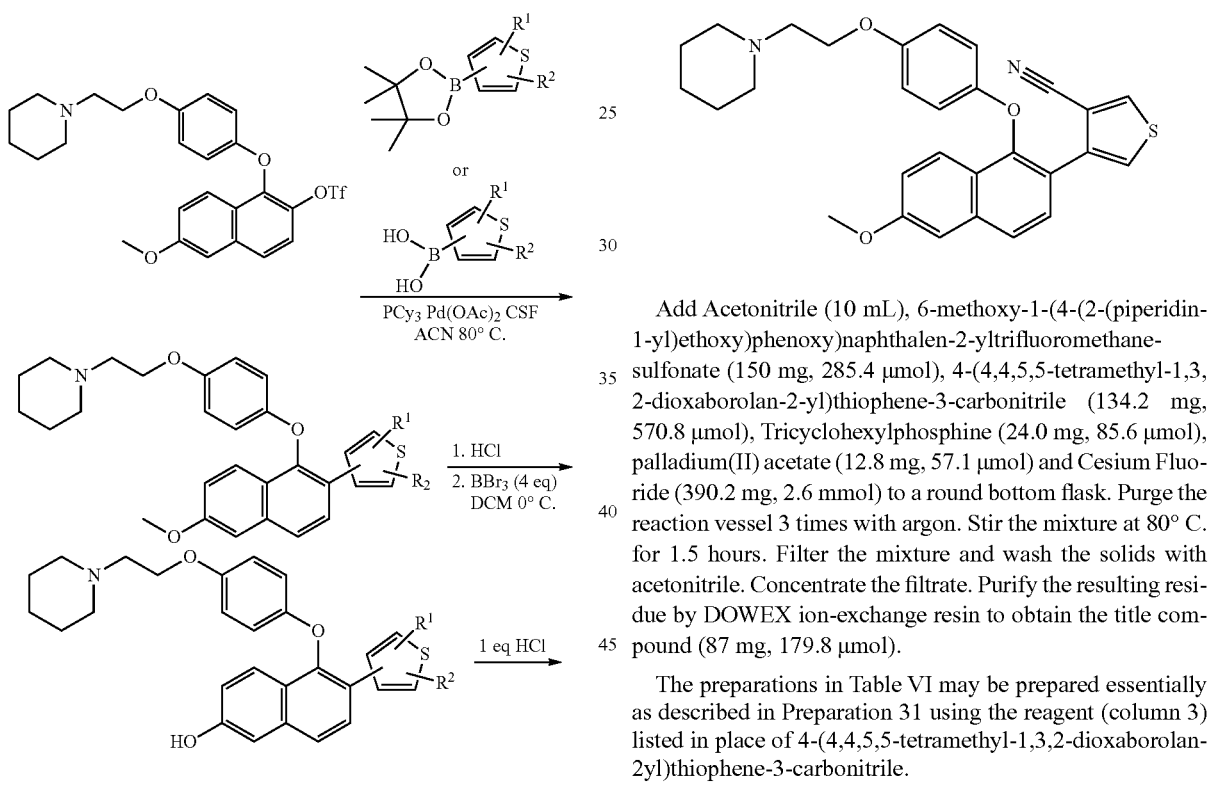

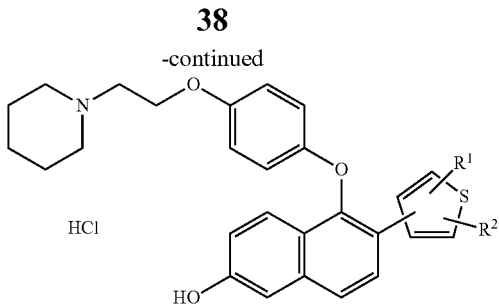

Preparation 31

4-(6-methoxy-1-(4-(2-(piperidin-1-yl)ethoxy)phenoxy)naphthalen-2-yl)thiophene-3-carbonitrile

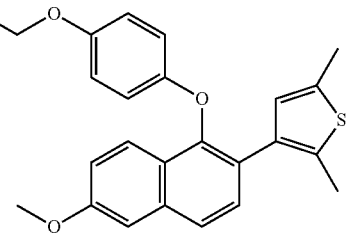

Add Acetonitrile (10 mL), 6-methoxy-1-(4-(2-(piperidin-1-yl)ethoxy)phenoxy)naphthalen-2-yltrifluoromethanesulfonate (150 mg, 285.4 μmol), 4-(4,4,5,5-tetramethyl-1,3,2-dioxaborolan-2-yl)thiophene-3-carbonitrile (134.2 mg, 570.8 μmol), Tricyclohexylphosphine (24.0 mg, 85.6 μmol), palladium(II) acetate (12.8 mg, 57.1 μmol) and Cesium Fluoride (390.2 mg, 2.6 mmol) to a round bottom flask. Purge the reaction vessel 3 times with argon. Stir the mixture at 80° C. for 1.5 hours. Filter the mixture and wash the solids with acetonitrile. Concentrate the filtrate. Purify the resulting residue by DOWEX ion-exchange resin to obtain the title compound (87 mg, 179.8 μmol).

The preparations in Table VI may be prepared essentially as described in Preparation 31 using the reagent (column 3) listed in place of 4-(4,4,5,5-tetramethyl-1,3,2-dioxaborolan-2yl)thiophene-3-carbonitrile.

TABLE VI

| Preparation | Structure and Chemical Name | Reagent |
|---|---|---|
| 32 | 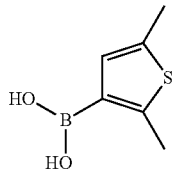<br>1-(2-(4-(2-(2,5-dimethylthiophen-3-yl)-6-methoxynaphthalen-1-yloxy)phenoxy-ethyl)piperidine | (structure shown) |

TABLE VI-continued

| Preparation | Structure and Chemical Name | Reagent |
|---|---|---|
| 33 | 1-(2-(4-(6-methoxy-2-(4-methylthiophen-3-yl)naphthalen-1-yloxy)phenoxy)ethyl)piperidine | |
| 34 | 1-(4-(6-methoxy-1-(4-(2-(piperidin-1-yl)ethoxy)phenoxy)naphthalen-2-yl)thiophen-2-yl)ethanone | |

Preparation 35

4-(6-methoxy-1-(4-(2-(piperidin-1-yl)ethoxy)phenoxy)naphthalen-2-yl)thiophene-3-carbonitrile hydrochloride

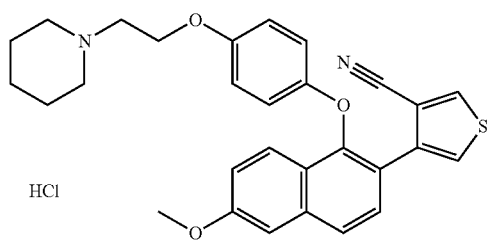 [SMILES: COc1ccc2c(Oc3ccc(OCCN4CCCCC4)cc3)c(-c3cscc3C#N)ccc2c1 ; Cl]

Add a solution of Hydrogen Chloride in ether (1 M, 180 μL, 180.0 μmol) to a prepared solution of 4-(6-methoxy-1-(4-(2-(piperidin-1-yl)ethoxy)phenoxy)naphthalen-2-yl)thiophene-3-carbonitrile (87 mg, 179.5 μmol) in Dichloromethane (2 mL). Stir the mixture for 10 min. Concentrate the mixture to obtain the title compound (95 mg, 179 μmol).

The preparations in Table VII may be prepared essentially as described in Preparation 35 using the reagent (column 3) listed in place of 4-(6-methoxy-1-(4-(2-(piperidin-1-yl)ethoxy)phenoxy)naphthalen-2-yl)thiophene-3-carbonitrile.

TABLE VII

| Preparation | Chemical Name | Reagent |
|---|---|---|
| 36 | 1-(2-(4-(2-(2,5-dimethylthiophen-3-yl)-6-methoxynaphthalen-1-yloxy)phenoxy)ethyl)piperidine hydrochloride | Preparation 32 |
| 37 | 1-(2-(4-(6-methoxy-2-(4-methylthiophen-3-yl)naphthalen-1-yloxy)phenoxy)ethyl)piperidine hydrochloride | Preparation 33 |
| 38 | 1-(4-(6-methoxy-1-(4-(2-(piperidin-1-yl)ethoxy)phenoxy)naphthalen-2-yl)thiophen-2-yl)ethanone hydrochloride | Preparation 34 |

Preparation 39

4-(6-hydroxy-1-(4-(2-(piperidin-1-yl)ethoxy)phenoxy)naphthalen-2-yl)thiophene-3-carbonitrile

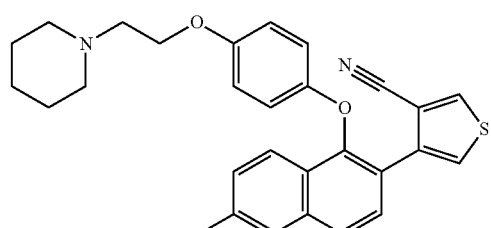

Slowly add boron tribromide in dichloromethane (4 M, 182 μL, 728.0 μmol) to a solution of 4-(6-methoxy-1-(4-(2-(piperidin-1-yl)ethoxy)phenoxy)naphthalen-2-yl)thiophene-3-carbonitrile hydrochloride (95 mg, 182.3 μmol) and dichloromethane (4 mL) stirring at 0° C. Stir the mixture at 0° C. for 1.5 hours. Quench the mixture with aqueous sodium bicarbonate. Extract the mixture 3 times with 20% methanol/dichloromethane. Wash the combined organic layers with water. Dry the resulting solution over sodium sulfate, filter, and concentrate to dryness. Purify the residue by flash chromatography on silica to obtain the title compound (52 mg, 111.2 μmol).

The preparations in Table VIII may be prepared essentially as described in Preparation 39 using the reagent (column 3) listed in place of 4-(6-methoxy-1-(4-(2-(piperidin-1-yl)ethoxy)phenoxy)naphthalen-2-yl)thiophene-3-carbonitrile hydrochloride.

TABLE VIII

| Preparation | Chemical Name | Reagent |
|---|---|---|
| 40 | 6-(2,5-dimethylthiophen-3-yl)-5-(4-(2-(piperidin-1-yl)ethoxy)phenoxy)naphthalen-2-ol | Preparation 36 |
| 41 | 6-(4-methylthiophen-3-yl)-5-(4-(2-(piperidin-1-yl)ethoxy)phenoxy)naphthalen-2-ol | Preparation 37 |
| 42 | 1-(4-(6-hydroxy-1-(4-(2-(piperidin-1-yl)ethoxy)phenoxy)naphthalen-2-yl)thiophen-2-yl)ethanone | Preparation 38 |

Alternate synthesis of Example 14

4-(6-hydroxy-1-(4-(2-(piperidin-1-yl)ethoxy)phenoxy)naphthalen-2-yl)thiophene-3-carbonitrile hydrochloride

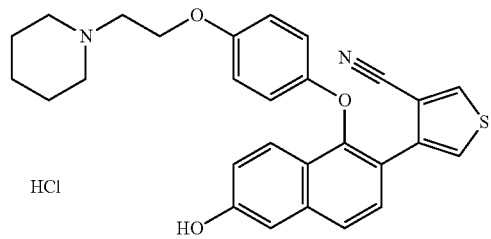 [SMILES: N#Cc1cscc1-c1ccc2cc(O)ccc2c1Oc1ccc(OCCN2CCCCC2)cc1 ; Cl]

Add a solution of hydrogen dichloride in ether (1 M, 122 μL, 122.0 μmol) to a solution of 4-(6-hydroxy-1-(4-(2-(piperidin-1-yl)ethoxy)phenoxy)naphthalen-2-yl)thiophene-3-carbonitrile (52 mg, 110.5 μmol) and dichloromethane (4 mL). Sonicate the mixture 5 minutes and then concentrate to obtain the title compound (57 mg, 110.5 μmol). MS (m/z): 471 (M+1-HCl).

The Examples in Table IX may be prepared essentially as described in the Alternate Synthesis of Example 14 using the reagent (column 3) listed in place of 4-(6-hydroxy-1-(4-(2-(piperidin-1-yl)ethoxy)phenoxy)naphthalen-2-yl)thiophene-3-carbonitrile.

TABLE IX

| Example | Preparation used in the HCl salt | Chemical Structure and Name | Mass Spectrum |
|---|---|---|---|
| Alternate synthesis of Example 15 | 40 | 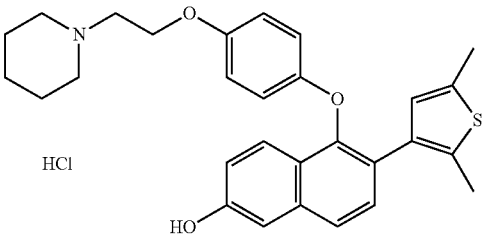<br>6-(2,5-dimethylthiophen-3-yl)-5-(4-(2-(piperidin-1-yl)ethoxy)phenoxy)naphthalen-2-ol hydrochloride | 474 (M + 1 − HCl) |
| Alternate synthesis of Example 11 | 41 | 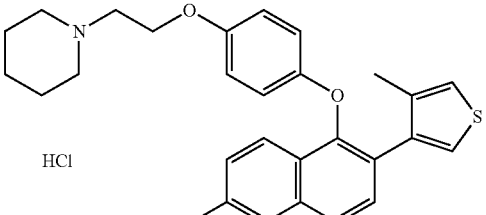<br>6-(4-methylthiophen-3-yl)-5-(4-(2-(piperidin-1-yl)ethoxy)phenoxy)naphthalen-2-ol hydrochloride | 460 (M + 1 − HCl) |

TABLE IX-continued

| Example | Preparation used in the HCl salt | Chemical Structure and Name | Mass Spectrum |
|---|---|---|---|
| Alternate synthesis of Example 10 | 42 | ![structure] 1-(4-(6-hydroxy-1-(4-(2-(piperidin-1-yl)ethoxy)phenoxy)naphthalen-2-yl)thiophen-2-yl)ethanone hydrochloride | 488 (M + 1 − HCl) |

Preparation 43

2-Bromo-4,5-dimethylthiophene

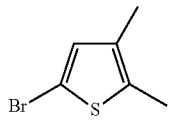

Add N-Bromosuccinimide (0.96 mg, 5.39 mmol) to a solution of 2,3-dimethylthiophene (0.55 g, 4.90 mmol) in dichloromethane (20 mL). Stir the reaction overnight. Concentrate the mixture. Purify the residue by flash chromatography on silica to obtain the title compound (704 mg, 3.68 mmol).

Preparation 44

2-bromo-3,5-dimethylthiophene

Preparation 44 may be prepared essentially as described in Preparation 43 using the reagent 2,4-dimethylthiophene.

Preparation 45

2-bromothiophene-3-carbonyl chloride

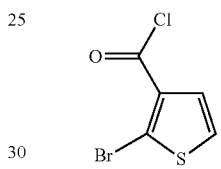

Add thionyl chloride (0.35 mL, 4.80 mmol) to a solution of 2-bromothiophene-3-carboxylic acid (500 mg, 2.41 mmol) and toluene (20 mL) with stirring. Purge the reaction vessel with nitrogen. Heat the mixture to reflux and stir for 3 hours. Concentrate the mixture to obtain the title compound (540 mg, 2.41 mmol). Use compound in next procedure without further purification.

Preparation 46

5-bromothiophene-3-carbonyl chloride

Preparation 46 may be prepared essentially as described in Preparation 45 using the reagent 5-bromothiophene-3-carboxylic acid.

Preparation 47

2-bromothiophene-3-carboxamide

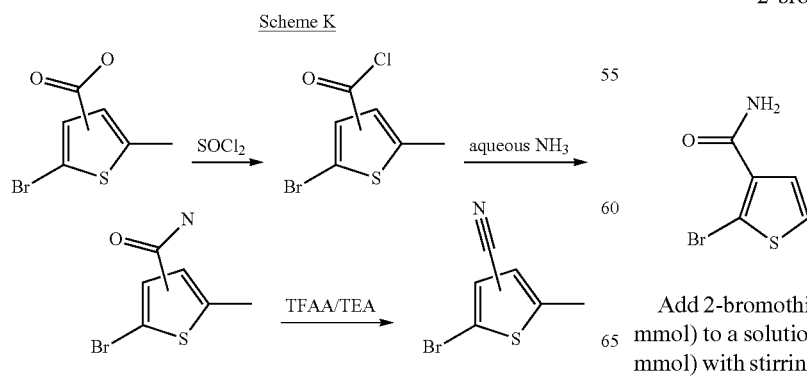

Add 2-bromothiophene-3-carbonyl chloride (540 mg, 2.39 mmol) to a solution of aqueous ammonia (25%, 3 mL, 17.44 mmol) with stirring. Stir the mixture for 30 minutes. Concentrate the mixture. Collect the resulting precipitate via filtration and wash the solids with water. Dry the white precipitate in vacuo to obtain the title compound (450 mg, 2.17 mmol).

Preparation 48

5-bromothiophene-3-carboxamide

Preparation 48 may be prepared essentially as described in Preparation 47 using the reagent 5-bromothiophene-3-carbonyl chloride.

Preparation 49

2-bromothiophene-3-carbonitrile

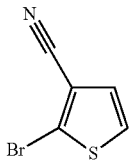

Add 2,2,2-trifluoroacetic anhydride (0.17 mL, 1.21 mmol) via syringe to a solution of 2-bromothiophene-3-carboxamide (200 mg, 970.58 μmol) and triethylamine (0.34 mL, 2.44 mmol) in THF (10 ml) with stirring at 5° C. Remove the cooling bath and warm the mixture to room temperature and stir for 16 hours. Concentrate the mixture. Add water and dichloromethane. Extract the mixture 3 times with dichloromethane. Dry the combined extracts over sodium sulfate, filter, and concentrate to dryness. Purify the residue by flash chromatography on silica to obtain the title compound (113 mg, 601.76 μmol).

Preparation 50

5-bromothiophene-3-carbonitrile

Preparation 50 may be prepared essentially as described in Preparation 49 using the reagent 5-bromothiophene-3-carboxamide.

Scheme L

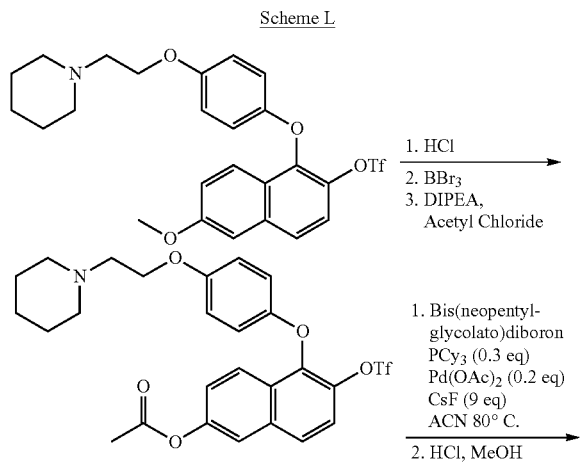

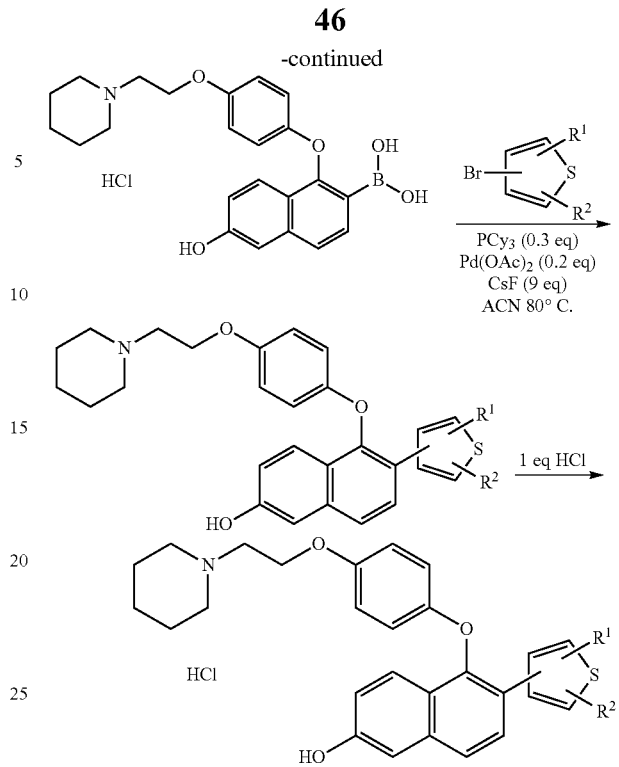

Preparation 51

6-methoxy-1-(4-(2-(piperidin-1-yl)ethoxy)phenoxy) naphthalen-2-yl trifluoromethanesulfonate hydrochloride Add a solution of hydrogen chloride in ether (1.0 M, 5.5 mL, 5.50 mmol) to a solution of 6-methoxy-1-(4-(2-(piperidin-1-yl)ethoxy)phenoxy)naphthalen-2-yl trifluoromethanesulfonate (2.62 g, 4.99 mmol) and dichloromethane (20 mL). Stir the mixture for 10 minutes and then concentrate to obtain the title compound (2.8 g, 4.99 mmol).

Preparation 52

6-hydroxy-1-(4-(2-(piperidin-1-yl)ethoxy)phenoxy) naphthalen-2-yl trifluoromethanesulfonate Add a solution of boron tribromide in dichloromethane (4 M, 5 mL, 20.00 mmol) to a solution of 6-methoxy-1-(4-(2-(piperidin-1-yl)ethoxy)phenoxy)naphthalen-2-yl trifluoromethanesulfonate hydrochloride (2.8 g, 4.98 mmol) and dichloromethane (100 ml). Stir the reaction for 2 hours and then quench with aqueous sodium bicarbonate. Extract the mixture 3 times with dichloromethane. Combine the extracts, dry over sodium sulfate, filter and concentrate to obtain the title compound (2.4 g, 4.68 mmol).

Preparation 53

5-(4-(2-(piperidin-1-yl)ethoxy)phenoxy)-6-(trifluoromethylsulfonyloxy)naphthalen-2-yl acetate Add acetyl chloride (0.67 mL, 9.41 mmol) to a solution of 6-hydroxy-1-(4-(2-(piperidin-1-yl)ethoxy)phenoxy)naphthalen-2-yl trifluoromethanesulfonate (2.4 g, 4.69 mmol) and diisopropylethylamine (2.45 mL, 14.05 mmol). Stir the mixture for 1 hour and then quench with aqueous sodium bicarbonate. Extract the mixture 3 times with dichloromethane. Combine the extracts, dry over sodium sulfate, filter, and concentrate to obtain the title compound (2.33 g, 4.22 mmol).

Preparation 54

6-hydroxy-1-(4-(2-(piperidin-1-yl)ethoxy)phenoxy)naphthalen-2-ylboronic acid hydrochloride

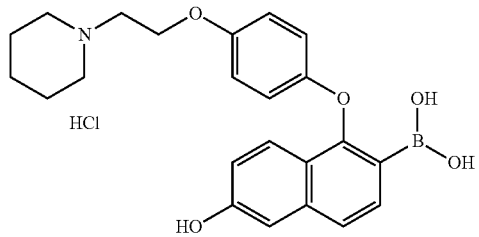 [SMILES: OB(O)c1ccc2cc(O)ccc2c1Oc1ccc(OCCN2CCCCC2)cc1 ; Cl]

Add bis(neopentyl glycolato)diboron (4.2 g, 18.59 mmol), 5-(4-(2-(piperidin-1-yl)ethoxy)phenoxy)-6-(trifluoromethylsulfonyloxy)naphthalen-2-yl acetate (2.33 g, 4.21 mmol), palladium (II) acetate (0.199 g, 886.38 μmol), cesium fluoride (5.21 g, 34.30 mmol), tricyclohexylphosphine (0.41 g, 1.40 mmol) and acetonitrile (50 mL) to a round bottom flask. Reflux the mixture with stirring for 1 hour under a nitrogen atmosphere. Cool the mixture, filter and wash the solids with acetonitrile. Concentrate the combined filtrate and washes. Suspend the resulting residue in diethyl ether (40 mL) and sonicated for 30 minutes. Remove the precipitate by filtration and concentrate the filtrate to obtain the crude intermediate. Add diethanolamine (405.25 μL, 4.21 mmol) to a solution of the crude intermediate in ether (50 mL). Stir the mixture for 1 hour. Decant the organic layer and dissolve the remaining residue in methanol (20 mL) and 10 mL of water. Add concentrated HCl (2 mL; 24 mmol) and stir the resulting mixture for 16 hours. Concentrate the mixture to remove MeOH. Extract the aqueous residue 3 times with dichloromethane. Combine the extracts, dry over sodium sulfate, filter, and concentrate to dryness. Purify the residue by flash chromatography on silica to obtain the title compound. (0.6 g, 1.47 mmol).

Preparation 55

3-(6-hydroxy-1-(4-(2-(piperidin-1-yl)ethoxy)phenoxy)naphthalen-2-yl)thiophene-2-carbonitrile

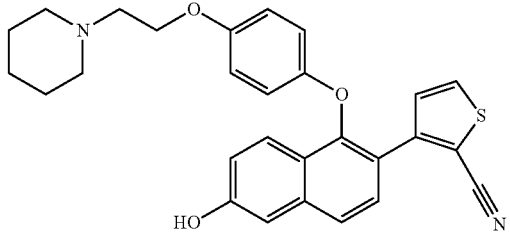 [SMILES: N#Cc1sccc1-c1ccc2cc(O)ccc2c1Oc1ccc(OCCN2CCCCC2)cc1]

Add 3-bromothiophene-2-carbonitrile (93 mg, 494.6 μmol), palladium (II) acetate (12 mg, 53.4 μmol), tricyclohexylphosphine (21 mg, 74.9 μmol), cesium fluoride (336 mg, 2.2 mmol) to a solution of 6-hydroxy-1-(4-(2-(piperidin-1-yl)ethoxy)phenoxy)naphthalen-2-ylboronic acid hydrochloride (100 mg, 245.5 μmol) in ethanol (2 mL), and acetonitrile (8 mL). Purge the reaction vessel 3 times with nitrogen. Stir the mixture at 85° C. for 2 hours. Cool the mixture and filter. Wash the resulting solids with acetonitrile. Concentrate the combined filtrate and washes. Purify the residue by DOWEX ion exchange resin to obtain the crude product. Purify the crude product by Prep-HPLC to obtain the title compound (12 mg, 24.55 μmol).

The preparations in Table X may be prepared essentially as described in Preparation 55 using the reagent (column 3) listed in place of 3-bromothiophene-2-carbonitrile.

TABLE X

| Preparation | Chemical Name | Reagent |
|---|---|---|
| 56 | 4-(6-hydroxy-1-(4-(2-(piperidin-1-yl)ethoxy)phenoxy)naphthalen-2-yl)thiophene-2-carbonitrile | 4-bromothiophene-2-carbonitrile |
| 57 | 1-(3-(6-hydroxy-1-(4-(2-(piperidin-1-yl)ethoxy)phenoxy)naphthalen-2-yl)thiophen-2-yl)ethanone | 1-(3-bromo-2-thienyl)ethanone |
| 58 | 5-(4-(2-(piperidin-1-yl)ethoxy)phenoxy)-6-(5-(trifluoromethyl)thiophen-2-yl)naphthalen-2-ol | 2-bromo-5-(trifluoromethyl)thiophene |
| 59 | 2-(6-hydroxy-1-(4-(2-(piperidin-1-yl)ethoxy)phenoxy)naphthalen-2-yl)thiophene-3-carbonitrile | 2-bromothiophene-3-carbonitrile |
| 60 | methyl 3-(6-hydroxy-1-(4-(2-(piperidin-1-yl)ethoxy)phenoxy)naphthalen-2-yl)thiophene-2-carboxylate | methyl 3-bromothiophene-2-carboxylate |
| 61 | 6-(5-methylthiophen-3-yl)-5-(4-(2-(piperidin-1-yl)ethoxy)phenoxy)naphthalen-2-ol | 4-bromo-2-methyl-thiophene |
| 62 | 6-(3,5-dimethylthiophen-2-yl)-5-(4-(2-(piperidin-1-yl)ethoxy)phenoxy)naphthalen-2-ol | 2-bromo-3,5-dimethyl-thiophene |
| 63 | 6-(4,5-dimethylthiophen-2-yl)-5-(4-(2-(piperidin-1-yl)ethoxy)phenoxy)naphthalen-2-ol | 5-bromo-2,3-dimethyl-thiophene |

EXAMPLE 26

3-(6-hydroxy-1-(4-(2-(piperidin-1-yl)ethoxy)phenoxy)naphthalen-2-yl)thiophene-2-carbonitrile hydrochloride

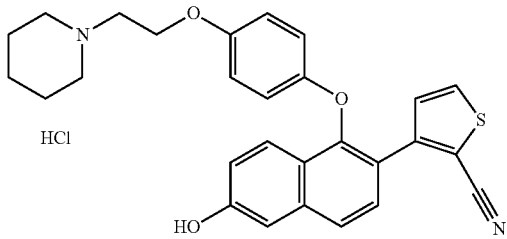 [SMILES: N#Cc1sccc1-c1ccc2cc(O)ccc2c1Oc1ccc(OCCN2CCCCC2)cc1 ; Cl]

Add a solution of hydrogen chloride in ether (1 M, 28 μL; 28.0 μmol) to a solution of 3-(6-hydroxy-1-(4-(2-(piperidin-1-yl)ethoxy)phenoxy)naphthalen-2-yl)thiophene-2-carbonitrile (12 mg, 24.5 μmol) and dichloromethane (4 mL). Sonicate the mixture for 5 minutes and then concentrate to obtain the title compound (13 mg, 24.5 μmol). Mass spectrum (m/z): 471 (M+1-HCl).

The Examples in Table XI may be prepared essentially as described in the Example 26 using the reagent (column 3) listed in place of 3-(6-hydroxy-1-(4-(2-(piperidin-1-yl)ethoxy)phenoxy)naphthalen-2-yl)thiophene-2-carbonitrile.

TABLE XI

| Example | Preparation used in the HCl salt formation | Chemical Structure and Name | Mass Spectrum (m/z) |
|---|---|---|---|
| 27 | 56 | 4-(6-hydroxy-1-(4-(2-(piperidin-1-yl)ethoxy)phenoxy)naphthalen-2-yl)thiophene-2-carbonitrile hydrochloride | 471 (M + 1 − HCl) |
| 28 | 57 | 1-(3-(6-hydroxy-1-(4-(2-(piperidin-1-yl)ethoxy)phenoxy)naphthalen-2-yl)thiophen-2-yl)ethanone hydrochloride | 488 (M + 1 − HCl) |
| 29 | 58 | 5-(4-(2-(piperidin-1-yl)ethoxy)phenoxy)-6-(5-(trifluoromethyl)thiophen-2-yl)naphthalen-2-ol hydrochloride | 514 (M + 1 − HCl) |

TABLE XI-continued

| Example | Preparation used in the HCl salt formation | Chemical Structure and Name | Mass Spectrum (m/z) |
|---|---|---|---|
| 30 | 59 | 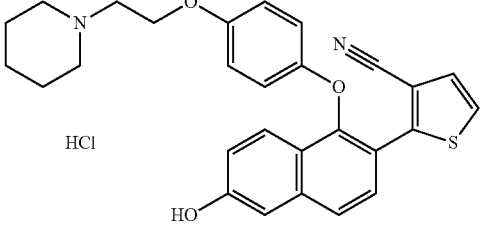<br>2-(6-hydroxy-1-(4-(2-(piperidin-1-yl)ethoxy)phenoxy)naphthalen-2-yl)thiophene-3-carbonitrile hydrochloride | 471 (M + 1 − HCl) |
| 31 | 60 | 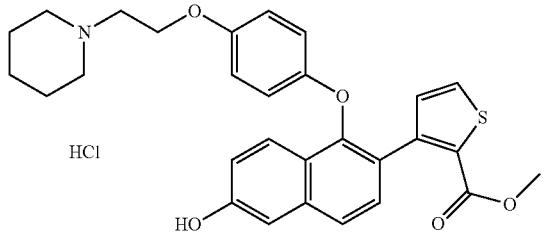<br>methyl 3-(6-hydroxy-1-(4-(2-(piperidin-1-yl)ethoxy)phenoxy)naphthalen-2-yl)thiophene-2-carboxylate hydrochloride | 504 (M + 1 − HCl) |
| 32 | 61 | 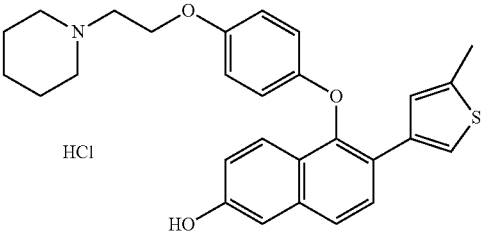<br>6-(5-methylthiophen-3-yl)-5-(4-(2-(piperidin-1-yl)ethoxy)phenoxy)naphthalen-2-ol hydrochloride | 460 (M + 1 − HCl) |
| 33 | 62 | 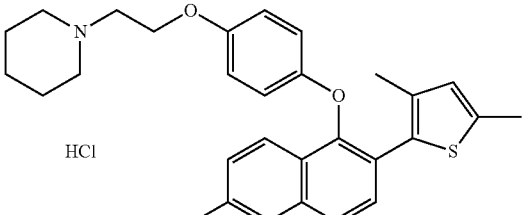<br>6-(3,5-dimethylthiophen-2-yl)-5-(4-(2-(piperidin-1-yl)ethoxy)phenoxy)naphthalen-2-ol hydrochloride | 474 (M + 1 − HCl) |
| 34 | 63 | 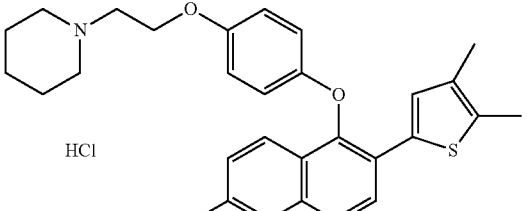<br>6-(4,5-dimethylthiophen-2-yl)-5-(4-(2-(piperidin-1-yl)ethoxy)phenoxy)naphthalen-2-ol hydrochloride | 474 (M + 1 − HCl) |

Scheme M

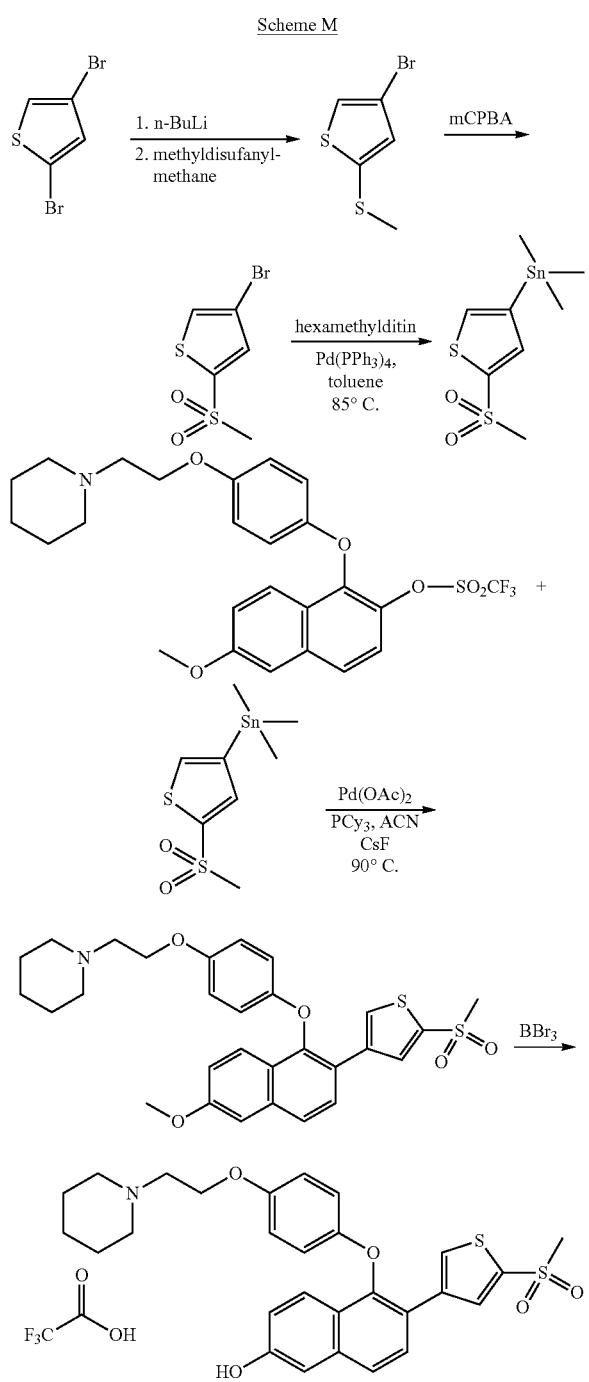

Preparation 64

Trimethyl-(5-methylsulfonyl-3-thienyl)stannane

Add n-butyl lithium (1.6M in Hexanes, 39 mL, 62 mmol) to a solution of 2,4-dibromothiophene (7 mL, 62 mmol) in ether (240 mL) at −78° C. After 0.5 hours, add n-butyl lithium (1.6M in Hexanes, 15.6 mL, 25 mmol) and stir the reaction for an additional 15 minutes at −78° C. Add methyldisulfanyl-methane (6 mL, 68 mmol) and stir the reaction while allowing to warm to room temperature. Pour the reaction into an ice saturated aqueous ammonium chloride mixture. Separate the layers and extract the aqueous layer with ether. Combine the organic layers and wash with saturated aqueous ammonium chloride, water and brine, then dry with sodium sulfate. Concentrate the resulting solution to obtain 4-bromo-2-methyl-sulfanyl-thiophene (9.3 g, 44.4 mmol).

Dissolve 4-bromo-2-methylsulfanyl-thiophene (9.3 g, 44.4 mmol) in dichloromethane (230 mL) and cool to 0° C. Add meta-chloro-perbenzoic acid (28 g, 162 mmol) in three portions at 5 minute intervals. Stir the resulting mixture while allowing it to warm to room temperature. Dilute the reaction with ether and wash with 5% aqueous sodium sulfite, saturated aqueous sodium bicarbonate and brine, then dry with sodium sulfate. Concentrate the resulting solution and purify the residue by flash chromatography (10-20% ethyl acetate in hexanes) to obtain 4-bromo-2-methylsulfonyl-thiophene (5 g, 20.73 mmol).

Dissolve 4-bromo-2-methylsulfonyl-thiophene (0.6 g, 2.5 mmol) in toluene (18 mL). Add hexamethylditin (1.8 mL, 3.8 mmol) and tetrakis(triphenylphosphino)palladium (0) (0.05 g, 0.04 mmol). Warm the resulting mixture to 85° C. and stir for 4 hours. Cool the mixture to room temperature and partition with brine. Concentrate the organic solution and purify by flash chromatography (0-10% ethyl acetate in hexanes) to obtain trimethyl-(5-methylsulfonyl-3-thienyl)stannane (0.5 g, 1.53 mmol).

Preparation 65

1-[2-[4-[[6-methoxy-2-(5-methylsulfonyl-3-thienyl)-1-naphthyl]oxy]phenoxy]ethyl]piperidine

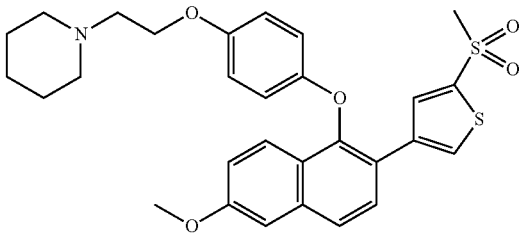 [SMILES: COc1ccc2c(Oc3ccc(OCCN4CCCCC4)cc3)c(-c3csc(S(C)(=O)=O)c3)ccc2c1]

Combine palladium(II)acetate (0.043 g 0.19 mmol) and trycyclohexylphosphine (0.081 g, 0.29 mmol) in acetonitrile (15 mL) and sonicate for 10 minutes. Add [6-methoxy-1-[4-[2-(1-piperidyl)ethoxy]phenoxy]-2-naphthyl]trifluo-romethanesulfonate (0.5 g, 0.95 mmol), trimethyl-(5-methylsulfonyl-3-thienyl)stannane (0.94 g, 2.9 mmol) and palladium mixture to a suspension of cesium fluoride (0.5 g, 3.3 mmol) in acetonitrile (40 mL). Warm the resulting mixture to 90° C. and stir for 18 hours. Cool the mixture to room temperature and concentrate. Partition the resulting residue between ethylacetate and saturated aqueous sodium bicarbonate. Separate the layers and wash the organic layer with saturated aqueous ammonium chloride and brine, then dry with sodium sulfate. Concentrate the resulting solution and purify by flash chromatography (0-5% methanol in dichloromethane) to obtain the title compound (0.3 g, 0.55 mmol).

EXAMPLE 35

6-(5-methylsulfonyl-3-thienyl)-5-[4-[2-(1-piperidyl)ethoxy]phenoxy]naphthalen-2-ol trifluoroacetate

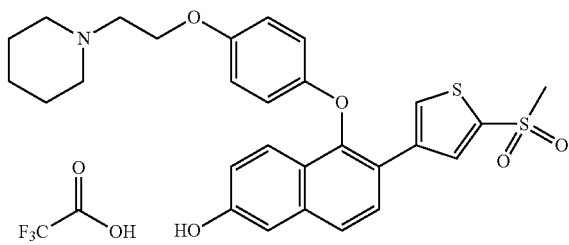 [SMILES: CS(=O)(=O)c1cc(-c2ccc3cc(O)ccc3c2Oc2ccc(OCCN3CCCCC3)cc2)cs1 ; O=C(O)C(F)(F)F]

Dissolve 1-[2-[4-[[6-methoxy-2-(5-methylsulfonyl-3-thienyl)-1-naphthyl]oxy]phenoxy]ethyl]piperidine (0.3 g, 0.55 mmol) in ethyl acetate. Add ether (10 mL) and cool to 0° C. Add hydrochloric acid (2M in ether, 0.4 mL, 0.84 mmol) and collect the resulting precipitate by filtration. Dissolve the solids in ethylacetate and concentrate to obtain 1-[2-[4-[[6-methoxy-2-(5-methylsulfonyl-3-thienyl)-1-naphthyl]oxy]phenoxy]ethyl]piperidine hydrochloride (0.35 g, 0.55 mmol).

Dissolve 1-[2-[4-[[6-methoxy-2-(5-methylsulfonyl-3-thienyl)-1-naphthyl]oxy]phenoxy]ethyl]piperidine hydrochloride (0.35 g 0.55 mmol) in dichloromethane (15 mL) and cool to 0° C. Add borontribromide (0.3 mL, 3.1 mmol) to the resulting cooled solution. Stir the resulting mixture for 1 hour at 0° C. Partition the reaction between ethylacetate and saturated aqueous sodium bicarbonate. Separate the layers and extract the aqueous layer with ethyl acetate (×2). Wash the combined organic layers with brine and dry with sodium sulfate. Concentrate the resulting solution and purify by high pressure liquid chromatography to obtain the title compound (24 mg, 0.04 mmol). Mass Spec (m/z): 524 (m+1-TFA).

Scheme N

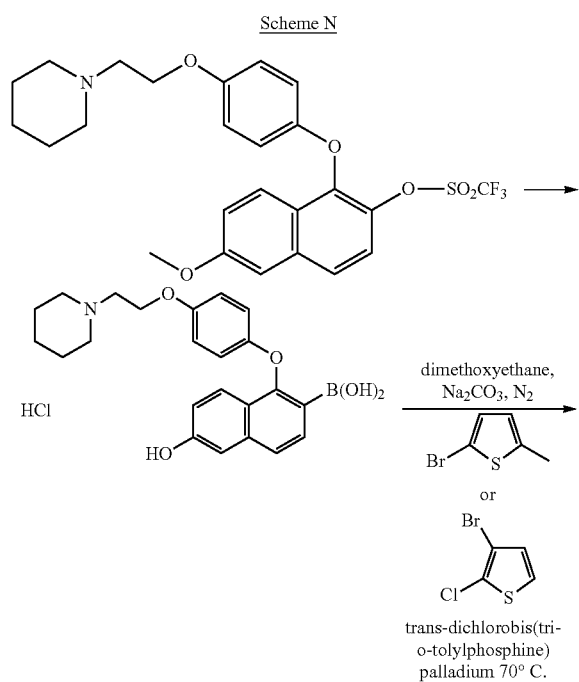

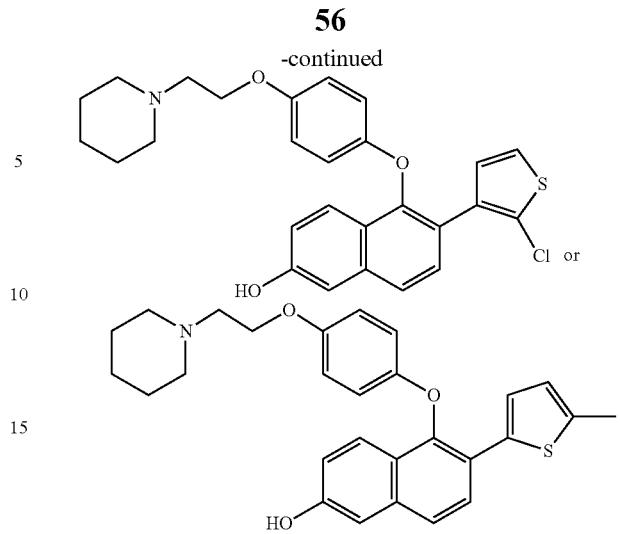

In Scheme N, the trifluoromethanesulfonate compound is converted to the boronic acid compound. The 6-boronic acid-5-[4-(2-piperidin-1-yl-ethoxy)-phenoxy]-naphthalen-2-ol hydrochloride salt may be prepared according to the procedure in PCT publication number WO2005073204. Convert the boronic acid compound to the substituted thiophene compound using either the reagent 3-bromo-2-chloro-thiophene or 2-bromo-5-methyl-thiophene using a process substantially as described in WO2005073204.

EXAMPLE 36

6-(2-chloro-3-thienyl)-5-[4-[2-(1-piperidyl)ethoxy]phenoxy]naphthalen-2-ol trifluoroacetate

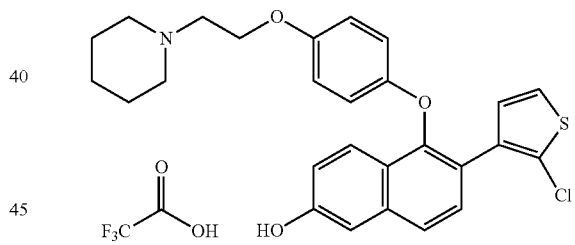

Prepare 6-(2-chloro-3-thienyl)-5-[4-[2-(1-piperidyl)ethoxy]phenoxy]naphthalen-2-ol trifluoroacetate essentially by the same procedure for preparing 5-[4-(2-piperidin-1-yl-ethoxy)-phenoxy]-6-(2,3,4-trifluoro-phenyl)-naphthalen-2-ol trifluoroacetate salt in WO2005073204 and using 3-bromo-2-chloro-thiophene. Mass Spec (m/z): 480 (M+1-TFA).

Scheme O
Alternate synthesis for the freebase form of Example 1

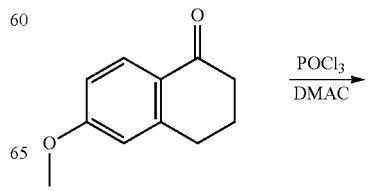

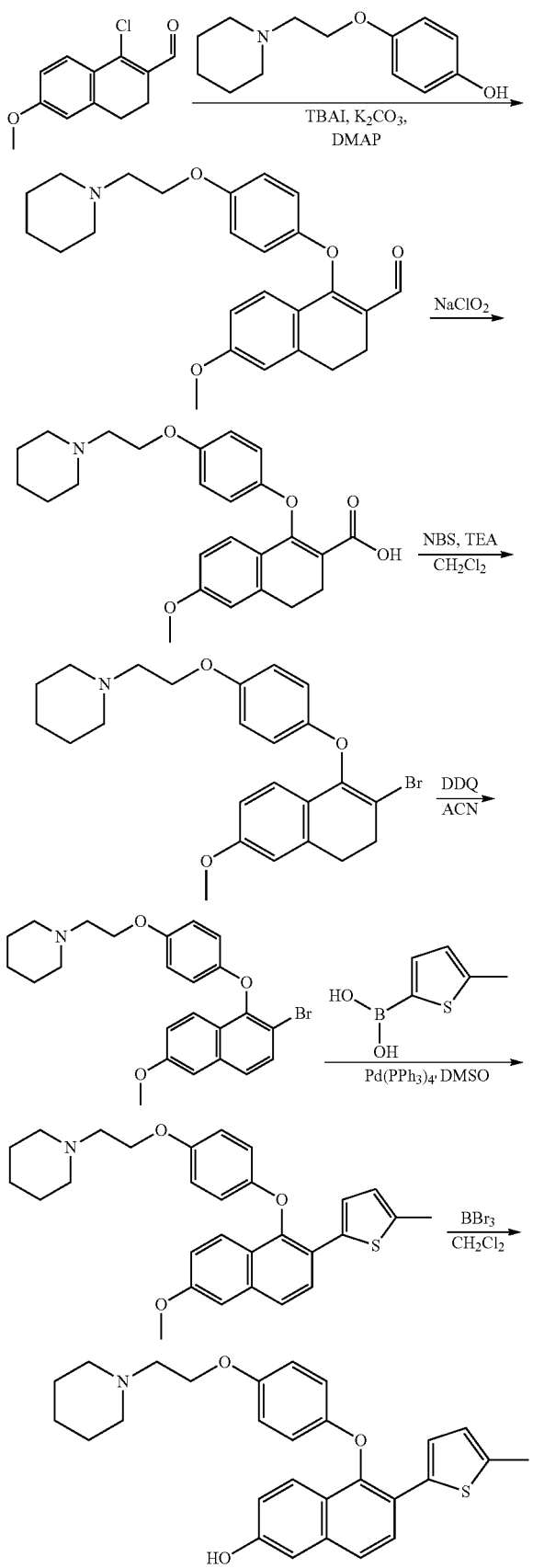

Preparation 69

1-Chloro-6-methoxy-3,4-dihydronaphthalene-2-carbaldehyde

To a round bottom flask, add compound 1 (of scheme 0; 6-methoxytetralin-1-one) (6.11 g, 34.7 mmol) and N,N-dimethylacetamide (20 mL, 259.5 mmol). Purge the reaction vessel with argon 5 times. Add POCl₃ (8 mL, 148.9 mmol) drop-wise to the reaction mixture. Heat the reaction mixture to 105° C. with stirring and hold the temperature for 4 hours. Quench the reaction mixture with ice-water. Extract the mixture with ethyl acetate three times and discard the aqueous phase. Combine the organic layers and dry over MgSO₄, filter, and concentrate to dryness to give 1-chloro-6-methoxy-3,4-dihydronaphthalene-2-carbaldehyde as a brown solid (5.94 g, 70% recovery).

Preparation 70

6-Methoxy-1-(4-(2-(piperidin-1-yl)ethoxy)phenoxy)-3,4-dihydronaphthalene-2-carbaldehyde To a 3-necked round bottom flask, add 1-chloro-6-methoxy-3,4-dihydronaphthalene-2-carbaldehyde (2.25 g, 10.1 mmol), 4-(2-(piperidin-1-yl)ethoxy)phenol (1.8 g, 8.24 mmol), tetra-N-butylammonium iodide (50 mg, 0.14 mmol), potassium carbonate (4.1 g, 29.8 mmol), and 4-dimethylaminopyridine (120 mg, 0.99 mmol). Purge the reaction vessel with nitrogen. Add dimethylformamide (30 mL) slowly to the reaction. Heat the mixture to 100° C. with stirring and hold for 4 hours. Cool the reaction mixture to room temperature and quench with ice-water. Extract the mixture with ethyl acetate three times. Dry the combined organic layers over MgSO₄, filter, and concentrate to give 6-methoxy-1-(4-(2-(piperidin-1-yl)ethoxy)phenoxy)-3,4-dihydronaphthalene-2-carbaldehyde (4.11 g).

Preparation 71

6-Methoxy-1-(4-(2-(piperidin-1-yl)ethoxy)phenoxy)-3,4-dihydronaphthalene-2-carboxylic acid To a round bottom flask, add 6-methoxy-1-(4-(2-(piperidin-1-yl)ethoxy)phenoxy)-3,4-dihydronaphthalene-2-carbaldehyde (3.0 g, 4.34 mmol), resorcinol (531 mg, 4.8 mmol), THF (8 mL), ethanol (8 mL) and acetic acid (0.9 mL). Stir the mixture at 25° C. for 5 min. Add slowly sodium chlorite (1.3 g, 11.2 mmol) in water (8 mL) to the reaction mixture. Stir the mixture at 80° C. for 2 hours. Quench the reaction mixture with ice-water. Add ethyl acetate to the vessel with stirring. Wash the mixture with dilute NaOH three times and discard the organic phase. To the aqueous layer, add water so the pH was adjusted to 5-6. Extract the aqueous layer with ethyl acetate five times and discard the aqueous phase. Dry the organic layer over MgSO₄, filter, and concentrate to dryness, which was further purified to give 400 mg of 6-methoxy-1-(4-(2-(piperidin-1-yl)ethoxy)phenoxy)-3,4-dihydronaphthalene-2-carboxylic acid. ¹HNMR (d-DMSO, 300 MHZ): 9.97 (1H, s) 7.12 (1H, m), 6.86 (5H, m), 6.71 (1H, m), 4.27 (2H, m), 3.73 (3H, s), 4.26 (2H, s), 3.41 (3H, m), 2.82 (2H, m), 2.59 (2H, m), 1.70 (6H, m).

Preparation 72

1-(2-(4-(2-Bromo-6-methoxy-3,4-dihydronaphthalen-1-yloxy)phenoxy)ethyl)piperidine To a flask, add 6-methoxy-1-(4-(2-(piperidin-1-yl)ethoxy)phenoxy)-3,4-dihydronaphthalene-2-carboxylic acid (0.4 g, 0.68 mmol), dichloromethane (10 mL), and triethylamine (0.2 mL, 1.43 mmol). Stir the mixture at 25° C. for 10 min. Add N-Bromosuccinimide (0.5 g; 4.13 equiv; 2.81 mmol) in portions. Cool the reaction mixture to room temperature and quench with ice-water. Extract the mixture with ethyl acetate three times and discard the aqueous phase. Dry the combined organic layers over $MgSO_4$, filter, and concentrate to dryness to give 1-(2-(4-(2-Bromo-6-methoxy-3,4-dihydronaphthalen-1-yloxy)phenoxy)ethyl)piperidine as a yellow oil (300 mg).

Preparation 73

1-(2-(4-(2-Bromo-6-methoxynaphthalen-1-yloxy)phenoxy)ethyl)piperidine

To a round bottom flask, add 1-(2-(4-(2-bromo-6-methoxy-3,4-dihydronaphthalen-1-yloxy)phenoxy)ethyl)piperidine (6.7 g, 6.6 mmol) and acetonitrile (50 mL). Stir the mixture at 25° C. for 5 min. Add 2,3-dichloro-5,6-dicyanobenzoquinone (DDQ) (3.2 g, 14.1 mmol) slowly to the reaction mixture. Heat the mixture to 80° C. and stir at the temperature for 14 hours. Cool the reaction mixture to room temperature and quench with ice-water. Extract the mixture with ethyl acetate three times and discard the aqueous phase. Dry the combined organic layers ($MgSO_4$), filter, and concentrate to dryness. Purify by flash chromatography to give 1-(2-(4-(2-bromo-6-methoxynaphthalen-1-yloxy)phenoxy)ethyl)piperidine as a brown solid (817 mg). $^1$HNMR (d-DMSO, 300 MHZ): 7.68 (3H, m), 7.43 (1H, s), 7.15 (1H, m), 6.97 (2H, d), 6.72 (2H, d), 4.26 (2H, s), 3.85 (3H, s), 3.48 (4H, m), 2.96 (2H, m), 1.70 (6H, m).

Preparation 74

1-(2-(4-(6-Methoxy-2-(5-methylthiophen-2-yl)naphthalen-1-yloxy)phenoxy)ethyl)piperidine To a 3-necked round bottom flask, add 1-(2-(4-(2-bromo-6-methoxynaphthalen-1-yloxy)phenoxy)ethyl)piperidine (25 mg, 75.9 µmol), 5-methylthiophen-2-ylboronic acid (20 mg, 140.86 µmol), tetrakis(triphenylphosphine)palladium (20 mg, 17.3 µmol), and dimethyl sulfone (DMSO) (2 mL). Purge the reaction vessel with nitrogen five times. Heat the mixture was at 100° C. for 6 hours, followed by 80° C. for 40 hours.

Preparation 75

6-(5-Methylthiophen-2-yl)-5-(4-(2-(piperidin-1-yl)ethoxy)phenoxy)naphthalen-2-ol

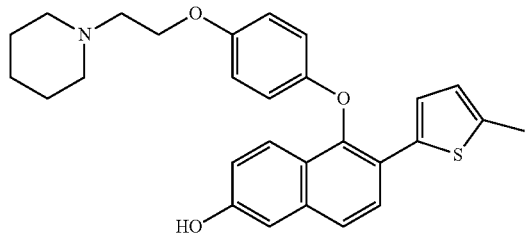 [SMILES: Cc1ccc(-c2ccc3cc(O)ccc3c2Oc2ccc(OCCN3CCCCC3)cc2)s1]

Deprotect 1-(2-(4-(6-methoxy-2-(5-methylthiophen-2-yl)naphthalen-1-yloxy)phenoxy)ethyl)piperidine using the procedure described in Example 1.

Biological Assays

Estrogen Receptor Binding Assay:

Compounds are tested for binding affinity to both estrogen receptor types (ERα and ERβ) by a competition binding assay that measures the compound's ability to displace $^3$H-estradiol from the receptors. $IC_{50}$ and $K_i$ values for both receptor types can be calculated.

A competition binding assay is run in a buffer containing 50 mM HEPES buffering reagent, pH 7.5, 1.5 mM ethylenediaminetetraacetic acid ("EDTA"), 150 mM NaCl, 10% glycerol, 1 mg/mL ovalbumin and 5 mM dithiothreitol ("DTT"), using 0.025 µCi per well $^3$H-Estradiol (NEN#NET517 at 118 Ci/mmol, 1 mCi/mL), 10 ng/well ERα or ERβ receptor. A test compound is added at 10 different concentrations. Non-specific binding is determined in the presence of 1 µM of estradiol (17 β-estradiol). The binding reaction (140 µL) is incubated for 4 hours at room temperature, then 70 µl of cold DCC buffer is added to each reaction (DCC buffer contains per 50 mL of assay buffer, 750 mg of charcoal and 250 mg of dextran). Plates are mixed 8 minutes on an orbital shaker at 4° C. Plates are then centrifuged at 3,000 rpm at 4° C. for 10 minutes. An aliquot of 120 µL of the mix is transferred to another 96-well, white flat bottom plate and 175 µL of scintillation fluid is added to each well. Plates are sealed and shaken vigorously on an orbital shaker. After an incubation of 2.5 hours, the plates are read in a counter. The data is used to calculate an $IC_{50}$ and % Inhibition at 10 µM. The $K_d$ for $^3$H-Estradiol is determined by saturation binding to ERα and ERβ receptors. The $IC_{50}$ values for test compounds are converted to $K_i$ using the Cheng-Prusoff equation, and the $K_d$ determined by saturation binding assay. All of the Examples disclosed herein demonstrate activity in the binding assay with a measured $K_i$-α of less than 20 nM for the ERα receptor and $K_1$-β of less than 200 nM for the ERβ receptor. For the compound of Example 1 the measured $K_i$-α was found to be 0.15±0.22 nM (geometric mean±standard deviation) while the affinity for the ERβ receptor was measured as $K_i$-β=0.20±0.20 nM (geometric mean±standard deviation). Thus, high-affinity binding of the compound of this invention to both ER receptors was demonstrated.

Ishikawa Cell Proliferation Assay:

This assay measures cell proliferation (using an alkaline phosphatase readout) in both an agonist mode in the presence of a test compound alone, and in an antagonist mode in which the ability of a test compound to block estradiol stimulation of growth is measured.

After an overnight incubation, Ishikawa cells are rinsed with Dulbecco's Phosphate Buffered Saline ("D-PBS") without $Ca^{+2}$ and $Mg^{+2}$, and trypsinized by a 3 minute incubation with 0.25% Trypsin/EDTA, phenol red-free. Cells are resuspended in assay medium and adjusted to 250,000 cells/mL. Approximately 25,000 cells in a 100 µl media are added to flat-bottom 96 wells microculture plates and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes.

For the agonist mode, plates receive 25 µL/well of assay medium followed by 25 µL/well of a diluted test compound (at 6× the final concentrations). For the antagonist mode, plates receive 25 µL/well of 6 nM 17 β-estradiol ("E2") followed by 25 µL/well of a diluted test compound (at 6× the final concentrations). After an additional 48-hour incubation at 37° C. in a 5% $CO_2$ humidified incubator, media is aspirated from wells and 100 µL fresh assay medium is added to each microculture. Serial dilutions of compounds are prepared and added to the cells as described above. After an additional 72 hour incubation at 37° C. in a 5% $CO_2$ humidified incubator, the assay is quenched by removing media and rinsing plates twice in D-PBS. The plates are dried for 5 minutes and frozen at −70° C. for at least 1 hour. The plates are then removed from the freezer and allowed to thaw at room temperature. After a 20-minute incubation, plates are read on a spectophotometer at 405 nm.

The data are fitted using a 4 parameter fit model to derive $EC_{50}$ (for agonist mode) or $IC_{50}$ (for antagonist mode) values. For the antagonist mode, a % efficacy for each compound is calculated versus E2 (1 nM) alone. For the agonist mode, a % efficacy for each compound is calculated versus the response to tamoxifen. The antagonist efficacy of the compound of Example 1, determined substantially as described above, was 102%±8.4% (n=4) (arithmetic mean±standard deviation); with a relative $IC_{50}$ of 3.75±1.71 nM (n=4) (geometric mean±standard deviation). The average agonist activity of the compound of Example 1 alone was 17.7%±11.3% (n=4) (arithmetic mean±standard deviation). The values for the compound of Example 1 may be compared to 4-hydroxytamoxifen which generally results in >100% agonist activity. These data show that this compound should act as an effective antagonist for the estrogen receptors in the uterus.

3-Day Immature Rat Uterus Antagonist Assay:

This model for uterine antagonism utilizes immature (3 week old) female rats that are highly sensitive to estrogenic stimulation of the uterus given that their circulating estrogen levels are prepubertal. The uteri from immature rats are fully responsive to exogenous estrogen, yet are quiescent in the absence of exogenous estrogen. Administration of exogenous estrogen to immature rats produces a reliable elevation of uterine weight, which can be used to study uterine antagonist effects. The rats are treated with both estradiol and 4 different concentrations of a test compound for 3 days and then uterine wet weights are measured.

Nineteen to twenty-one day old (or 45-50 g) female rats are orally treated with 17α-ethynylestradiol (EE2) (0.1 mg/kg, a maximal stimulatory estrogenic stimulus for reliably increasing uterine weight) and 10, 1.0, 0.1 and 0.01 mg/kg test compound for 3 days, 6 rats per group. Test compounds are dissolved in 20% β-hydroxycyclodextrin and administered by oral gavage in a volume of 0.2 mL daily (15 min. prior to EE2 gavage). A vehicle control, EE2 alone and EE2+raloxifene are also done as controls. The animals are fasted overnight following the final dose. On the following morning, the animals are weighed, then euthanized (by carbon dioxide asphyxiation) and the uteri rapidly collected (via a mid-line ventral incision) and weighed.

Uterine weight/body weight ratios (UWR) are calculated for each animal. The percent inhibition of the estrogen-induced response is then calculated by the following formula: percent inhibition=100×($UWR_{estrogen}$−$UWR_{test\ compound}$)/($UWR_{estrogen}$−$UWR_{control}$)

$ED_{50}$ values are derived from a semi-log regression analysis of the linear aspect of the dose response curve. Both the UWR data and the percent inhibition data are statistically analyzed by one way analysis of variance (ANOVA) with post-hoc testing by Fisher's PLSD when indicated by a p<0.05. The compound of Example 1 was observed to be a potent uterine antagonist using an assay substantially as described, with an $ED_{50}$ value of 0.053 mg/kg.

4-Day OVX Rat Uterine Agonist Assay:

In order to assure that a test compound does not have significant partial uterine agonist activity, compounds are administered to mature, ovariectomized rats.

Seventy-five day old rats are ovariectomized and treatment is started 14 days later when circulating estradiol levels have reached minimal levels. After 4 days of treatment with 3 doses of a test compound, (6 rats per group) body weight, uterine wet weight and uterine eosinophil peroxidase (EPO) activity are measured. Cholesterol levels are also measured to compare relative ability to lower cholesterol with other SERMs. If there is any question of uterine stimulation, histological examination will determine epithelial cell height.

A significant (>10% of the increase induced by estradiol @0.1 mg/kg) and dose-responsive increase in uterine EPO activity is used as an early indicator of potential uterine agonist activity. In comparison to the OVX group, the compound of Example 1, using an assay substantially as described at doses up to 10 mg/kg caused no significant dose related increases in EPO activity (Tukey Kramer; p<0.05). None of the groups dosed with the compound of Example 1 evidenced an increase in EPO activity that was >10% of that induced by estradiol at 0.1 mg/Kg. Significant, dose-related increases in uterine endometrial thickness have also been used as an early sign of potential SERM uterine agonist activity. In comparison to the OVX group the compound of Example 1 at doses up to 10 mg/kg did not result in significant, dose related increases in uterine endometrial thickness. These results suggest that the compound of Example 1 will provide desirable uterine safety.

OVX/Meniscal Tear Model

The rat meniscal tear (MCT) model is a well-described model of OA in which joint damage and pain are induced by surgical intervention (transection of the medial meniscus) in one knee joint. In the standard MCT model using male rats, joint pathology develops progressively and is measured via joint histology at 3 weeks post-surgery. An internal pilot study determined that at 5 weeks post-MCT surgery both pain and joint histopathology were significantly elevated in OVX/MCT animals in comparison to ovary-intact animals that underwent MCT surgery.

In OVX animals treated using a tear model substantially as described, a compound of Example 1 reduced pain in a dose-dependent fashion, and the reduction was statistically significant in comparison to the OVX/MCT group at all doses ≧1.0 mg/kg. In addition, doses of 3 and 10 mg/kg of Example 1 resulted in reductions in joint pain that were not statistically different from those induced by 17α-ethynylestradiol.

P-CTXII pCTX-II is believed to be a useful biomarker reflecting efficacy relating to the treatment of OA. See for example, Garnero P et al Ann Rheum Dis 2003; 62:939-943; Mazieres B et al, Arthritis Rheum 2003; 48:5683

The compound of Example 1 significantly and dose-dependently reduced pCTX-II. In addition, all doses of the Example 1 compound reduced pCTX-II to levels that were not statistically different from those resulting from treatment with 17α-ethynylestradiol.

We claim:

1. A compound of a formula

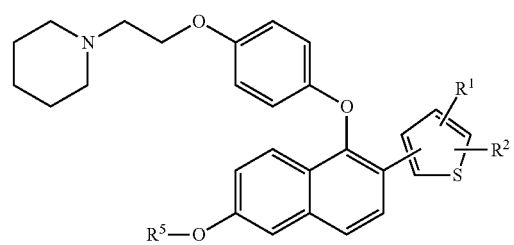

or a pharmaceutically acceptable salt thereof;

wherein
R¹ is selected from the group consisting of H, —C₁-C₄ alkyl, F, Cl, —CN, —C(O)R³, —(C₁-C₃ alkyl)OH, —OCH₃, —S(O)₂R⁴, —S(O)CH₃, —CF₃, and —S(C₁-C₃ alkyl);
R² is selected from the group consisting of H, F, and CH₃;
R³ is selected from the group consisting of OH, —OCH₃, —NH(C₀-C₂ alkyl), CH₃, —N(CH₃)₂;
R⁴ is selected from the group consisting of —C₁-C₄ alkyl, —N(CH₃)₂, and —CF₃; and
R⁵ is selected from the group consisting of H and CH₃.

2. A compound of claim 1 of the formula or a pharmaceutically acceptable salt thereof;
wherein
R¹ is selected from the group consisting of H, —C₁-C₄ alkyl, F, Cl, —CN, —C(O)R³, —(C₁-C₃ alkyl)OH, —OCH₃, —S(O)₂R⁴, —S(O)CH₃, and —S(C₁-C₃ alkyl);
R² is selected from the group consisting of H, F, and CH₃;
R³ is selected from the group consisting of OH, —OCH₃, —NH(C₀-C₂ alkyl), CH₃, —N(CH₃)₂;
R⁴ is selected from the group consisting of —C₁-C₄ alkyl, —N(CH₃)₂, and —CF₃; and
R⁵ is selected from the group consisting of H and CH₃.

3. A compound as claimed in claim 2 wherein R⁵ is H.

4. A compound as claimed in claim 3 wherein R² is selected from H and CH₃.

5. A compound as claimed in claim 4 wherein R² is H.

6. A compound as claimed in claim 1 wherein R¹ is selected from the group consisting of H, C₁-C₄ alkyl, F, Cl, CF₃, —CN, —C(O)R³, —S(O)₂R⁴, —S(O)CH₃, and —SCH₃.

7. A compound as claimed in claim 6 wherein R¹ is selected from the group consisting of H, —CH₃, —CH₂CH₃, —CH(CH₃)₂, —CH₂CH(CH₃)₂, F, Cl, —CF₃, —CN, —C(O)CH₃, —C(O)N(CH₃)₂, —S(O)₂CH(CH₃)₂, —S(O)₂CH₂CH₃, —S(O)₂CH₃, —S(O)CH₃, and —SCH₃.

8. A compound as claimed in claim 7 wherein R¹ is —CH₃.

9. A compound as claimed in claim 7 that is of the formula or a pharmaceutically acceptable salt thereof.

10. A compound as claimed in claim 7 that is of the formula or a pharmaceutically acceptable salt thereof.

11. A compound of claim 1 that is of formula or a pharmaceutically acceptable salt thereof.

12. A compound of claim 11 wherein the salt is the hydrochloride.

13. A pharmaceutical composition comprising a pharmaceutically acceptable carrier and at least one compound as claimed in claim 1.

14. A method for treating osteoarthritis in a mammal, comprising the step of administering to the mammal a compound as claimed in claim 11.

* * * * *